US 6,666,796 B1

(12) United States Patent
MacCready, Jr.

(10) Patent No.: US 6,666,796 B1
(45) Date of Patent: Dec. 23, 2003

(54) WALKING ASSISTING APPARATUS

(75) Inventor: Paul B. MacCready, Jr., Pasadena, CA (US)

(73) Assignee: Aerovironment, Inc., Monrovia, CA (US)

( * ) Notice: Subject to any disclaimer, the term of this patent is extended or adjusted under 35 U.S.C. 154(b) by 0 days.

(21) Appl. No.: 09/397,266

(22) Filed: Sep. 16, 1999

(51) Int. Cl.[7] .............................................. A63B 71/00
(52) U.S. Cl. .............................. 482/51; 482/66; 482/67; 482/75; 135/65; 135/67
(58) Field of Search ............................. 482/51, 66, 67, 482/74, 77, 75; 135/65, 66, 67; 601/35; 602/23, 16, 26, 27, 28, 29; 623/28, 27, 30, 33, 35, 38

(56) References Cited

U.S. PATENT DOCUMENTS

| 406,328 A | 7/1889 | Yagn | |
|---|---|---|---|
| 420,178 A | 1/1890 | Yagn | |
| 420,179 A | 1/1890 | Yagn | |
| 438,830 A | 10/1890 | Yagn | |
| 440,684 A | 11/1890 | Yagn | |
| 2,010,482 A | * 8/1935 | Cobb | ........................... 482/75 |
| 4,872,665 A | * 10/1989 | Chareire | ...................... 482/75 |
| 4,967,734 A | 11/1990 | Rennex | |
| 5,011,136 A | * 4/1991 | Rennex | ....................... 272/70 |
| 5,016,869 A | * 5/1991 | Dick et al. | .................... 482/75 |
| 5,020,790 A | * 6/1991 | Beard et al. | ................... 482/75 |

* cited by examiner

Primary Examiner—Nicholas D. Lucchesi
Assistant Examiner—Tam Nguyen
(74) Attorney, Agent, or Firm—William W. Haefliger

(57) ABSTRACT

Apparatus to assist human walking, incorporating in combination first and second longitudinally extending strut members that are relatively movable, longitudinally, and adapted to transmit body associated loading; the first strut member or members operatively connected to a rack and/or to the user's body; the second strut member or members slaved, i.e. operatively connected to the user's foot or feet, ankles or shoes, to move therewith; and a control that responds to step-by-step treading to control relative movement of the strut members. Such loading is controllably transferred back and forth between left and right pairs of strut members, in response to treading.

23 Claims, 20 Drawing Sheets

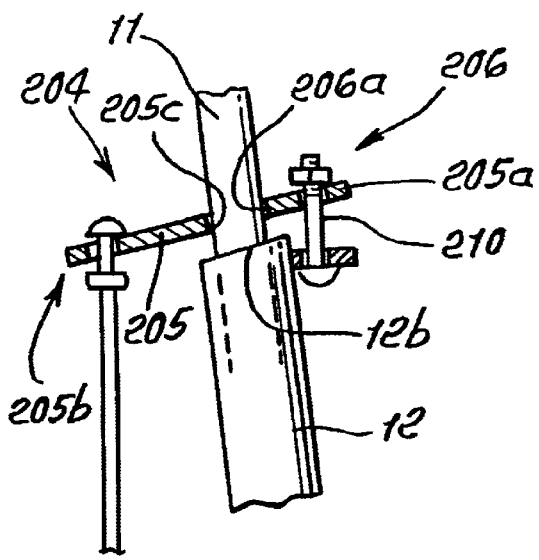
FIG. 5a.
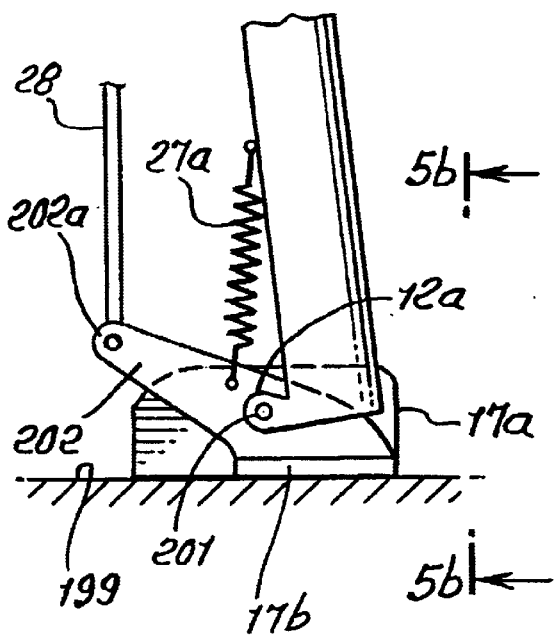
FIG. 5b.
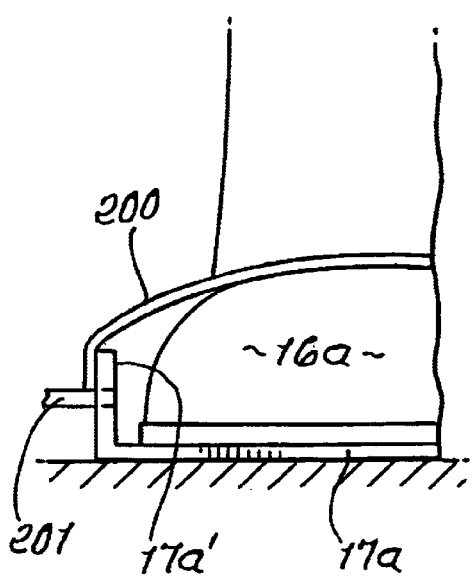

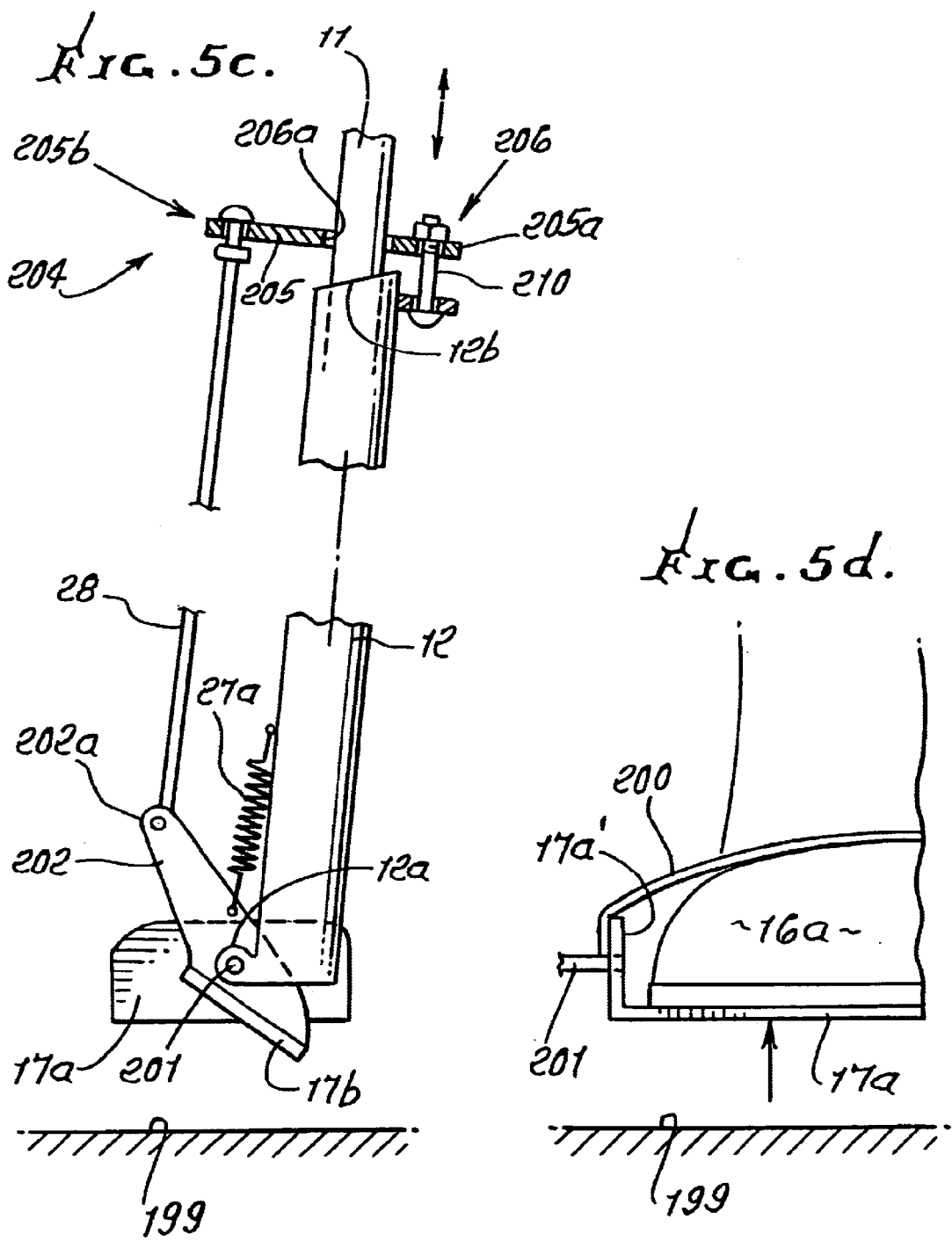

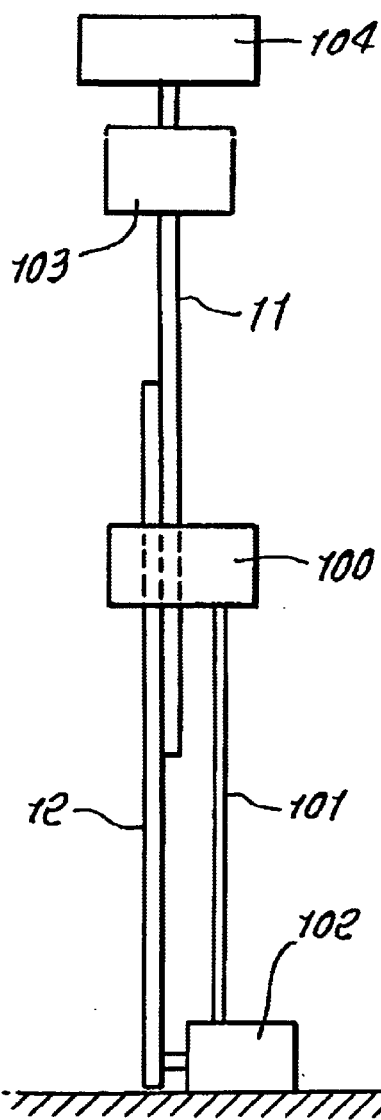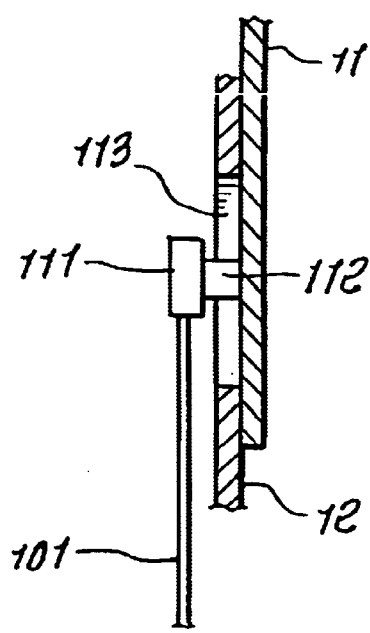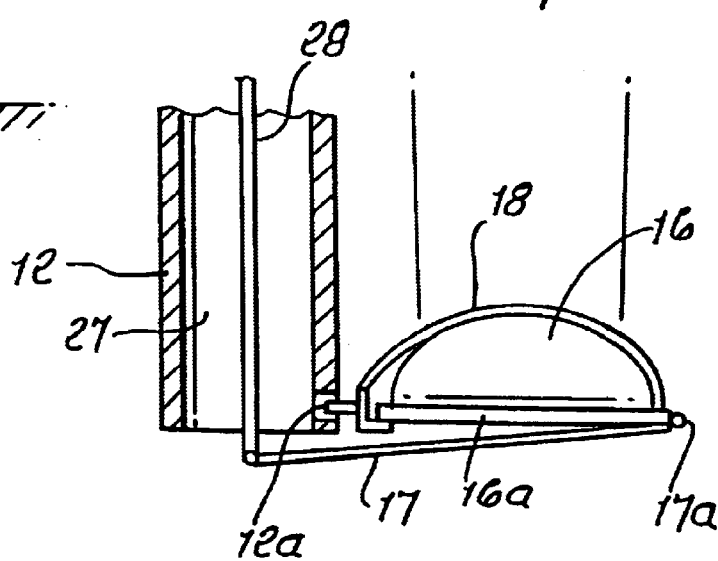

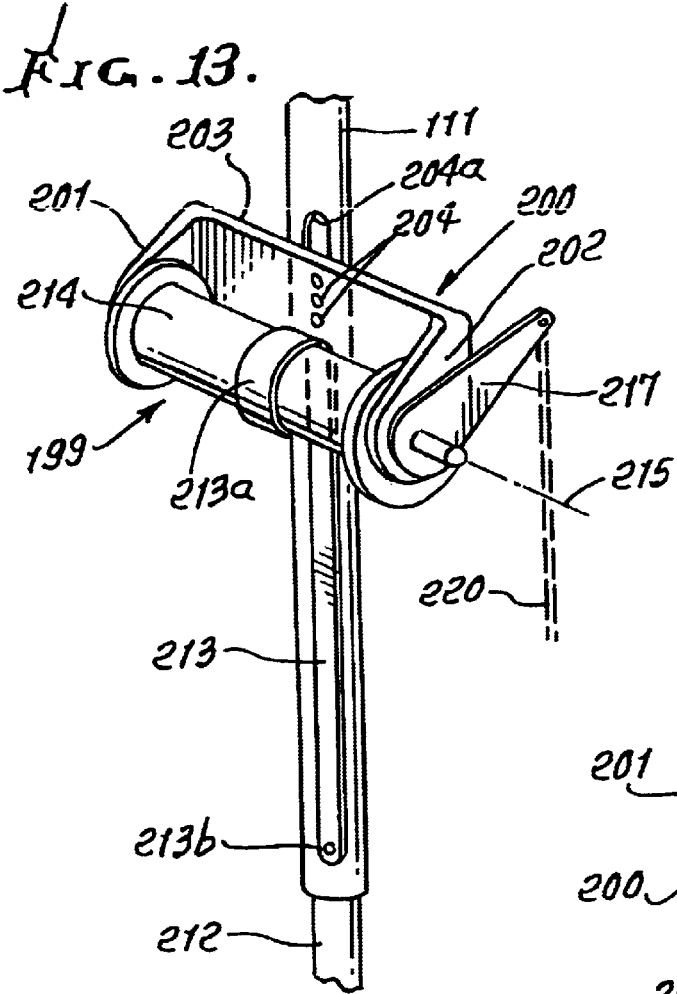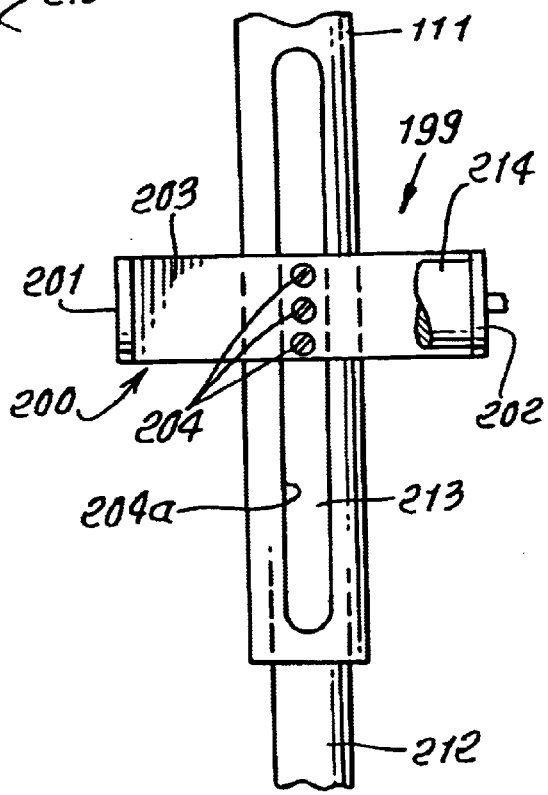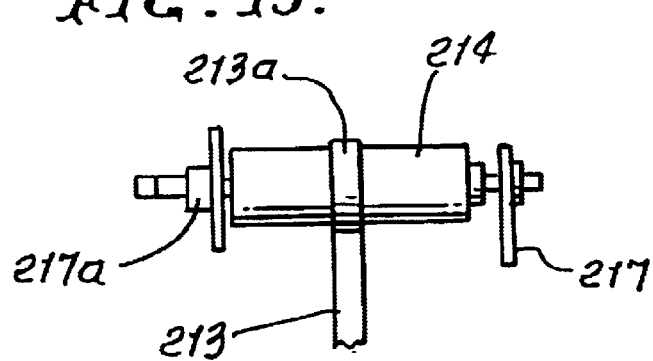

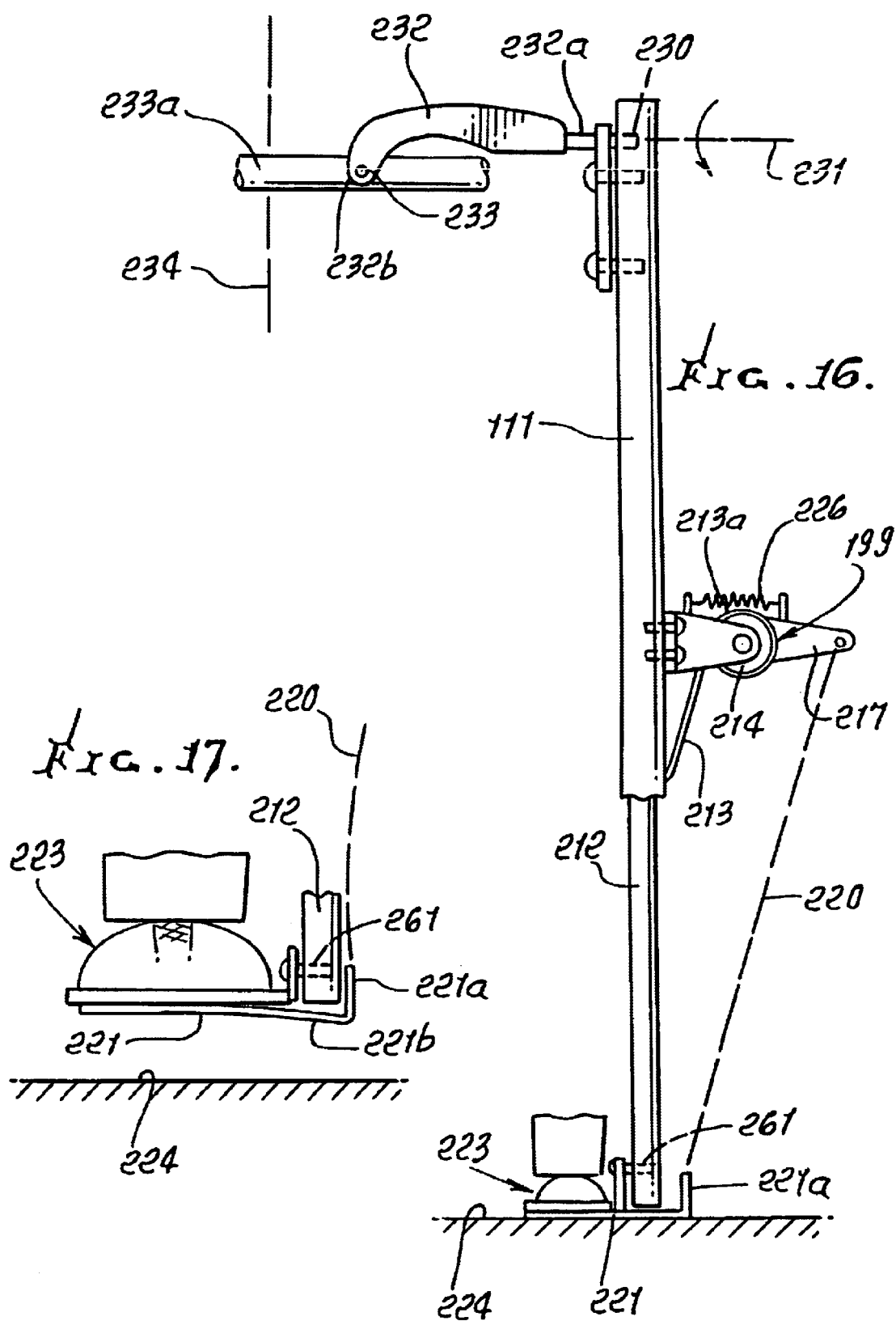

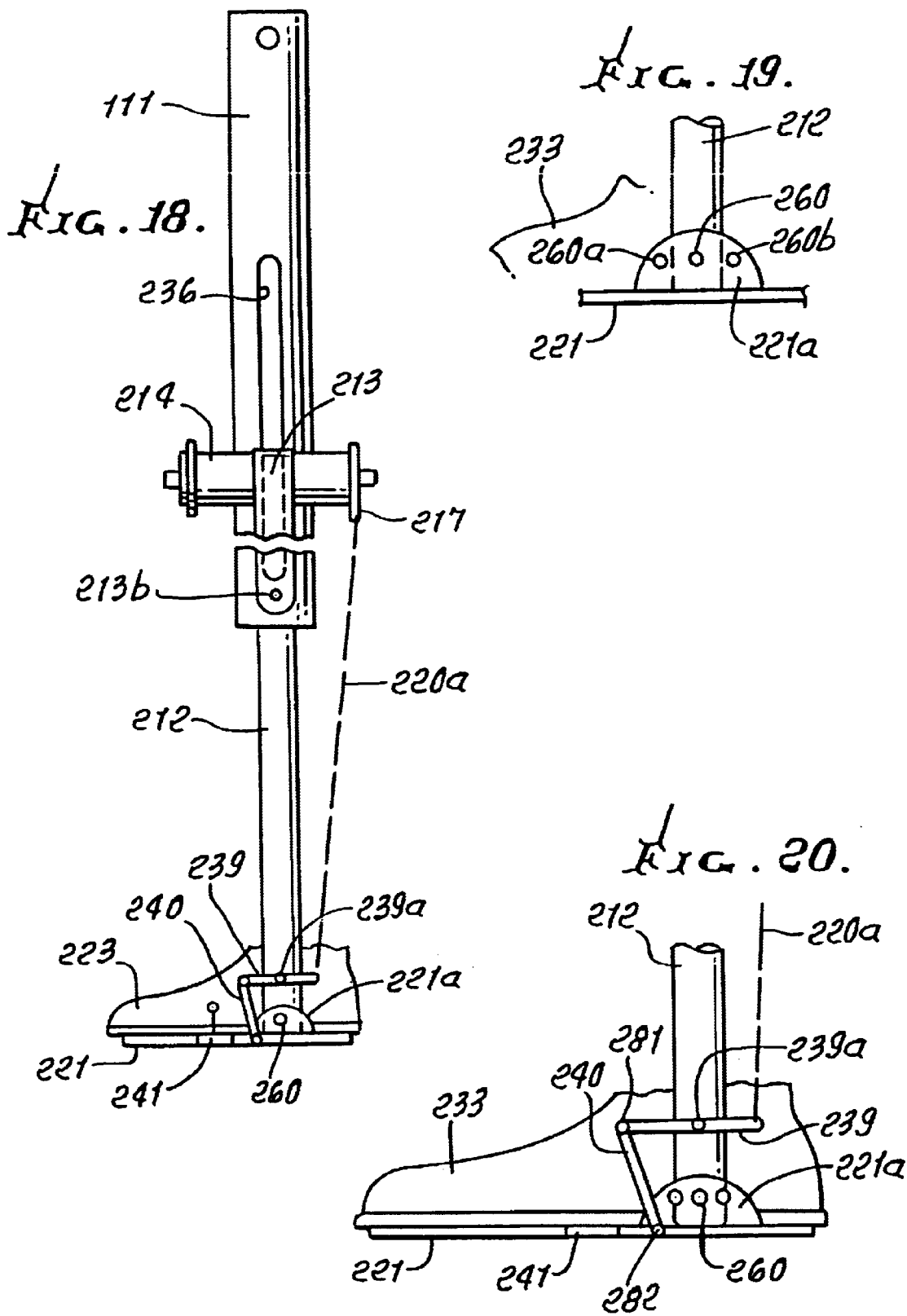

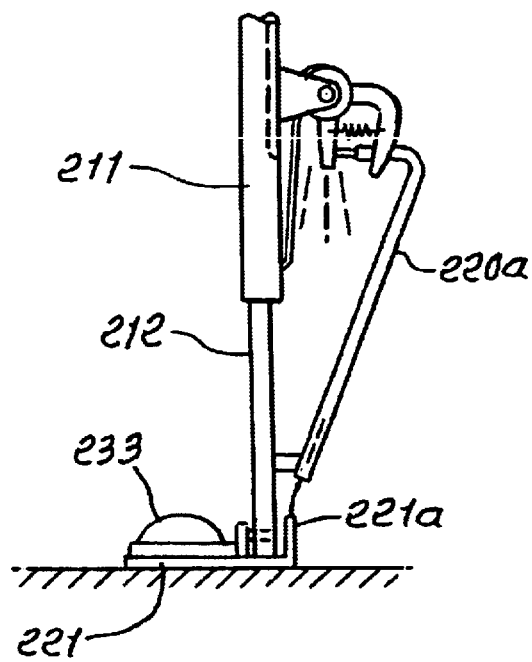
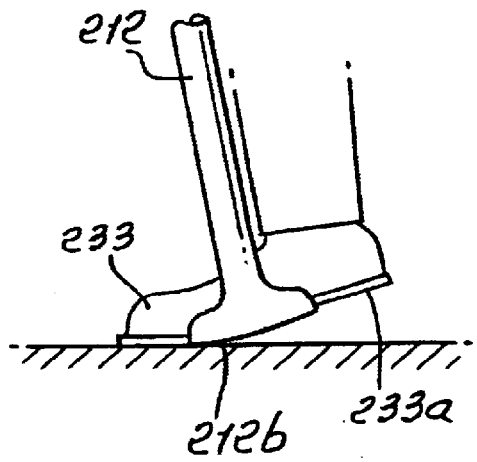
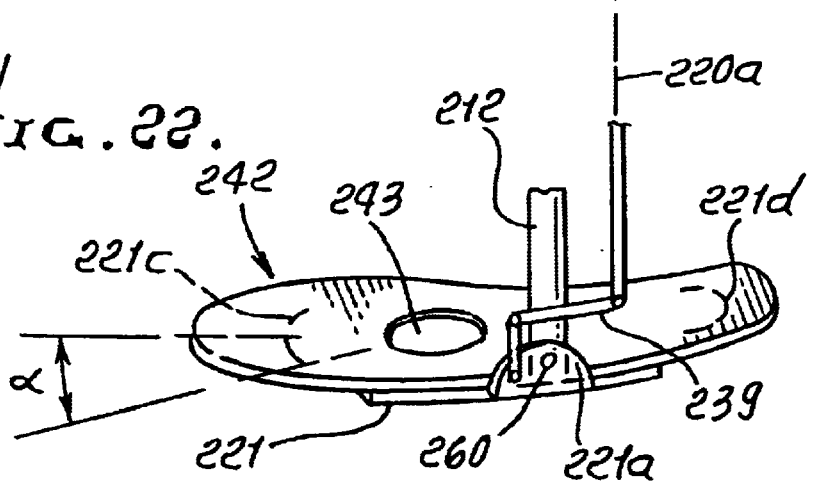

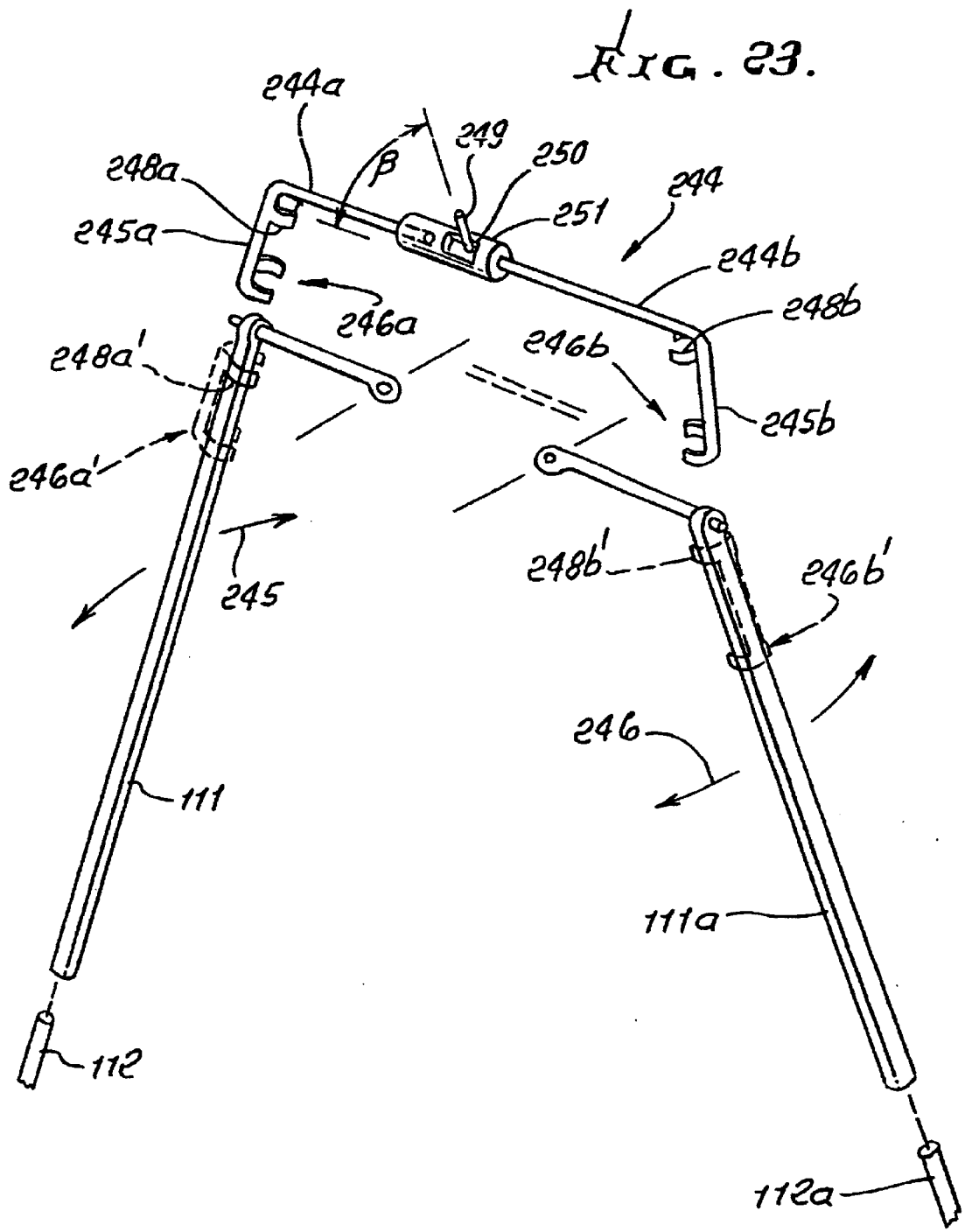

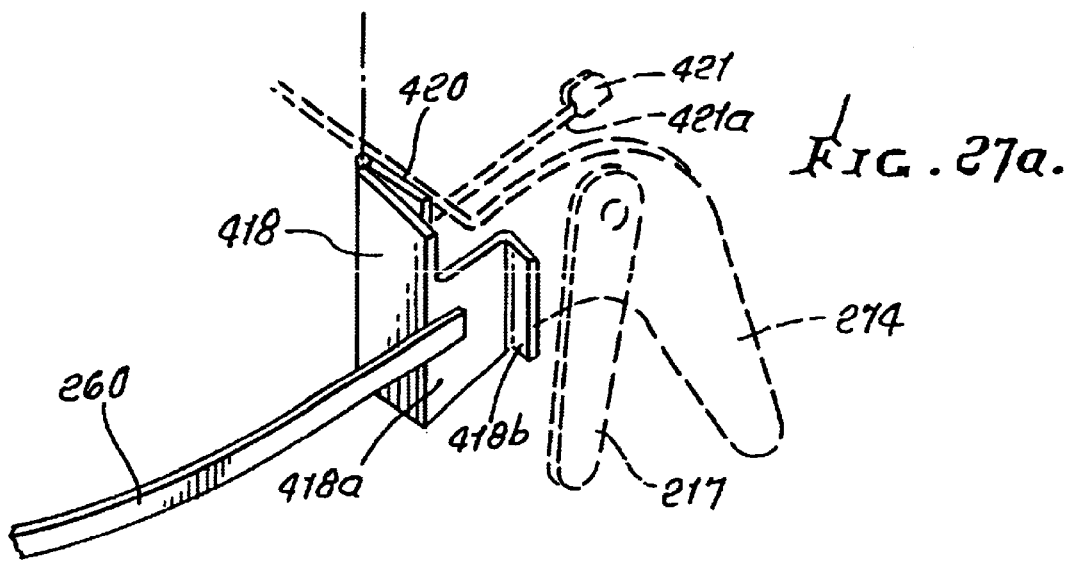
FIG. 27a.
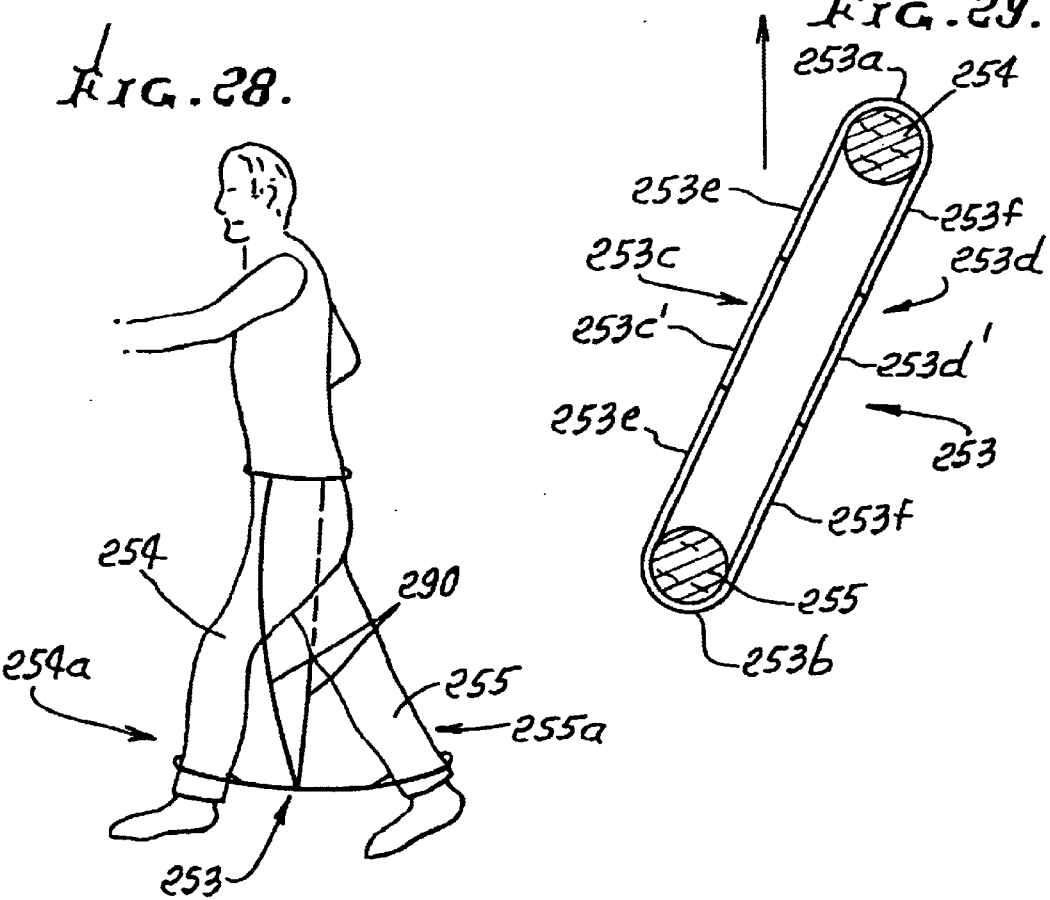
FIG. 28.
FIG. 29.

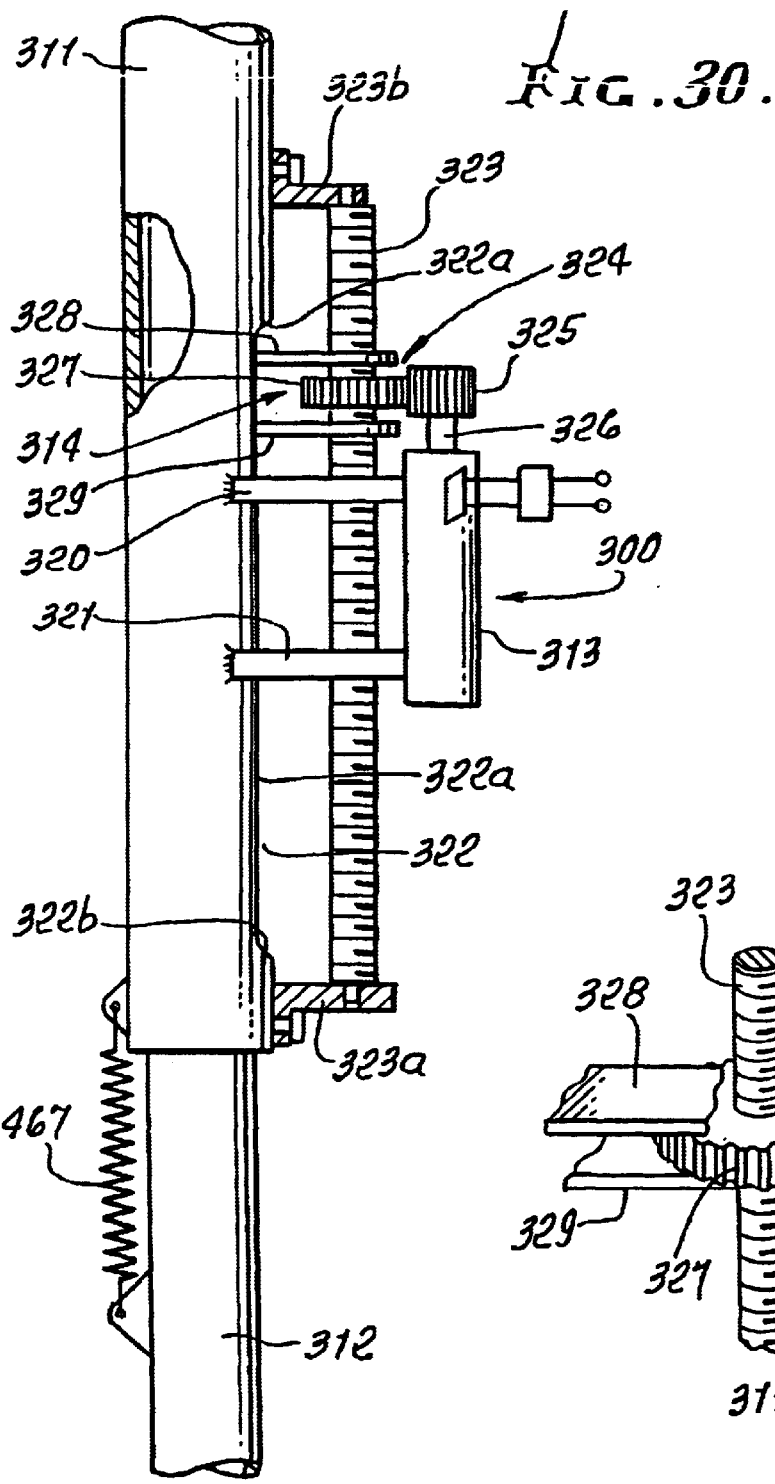
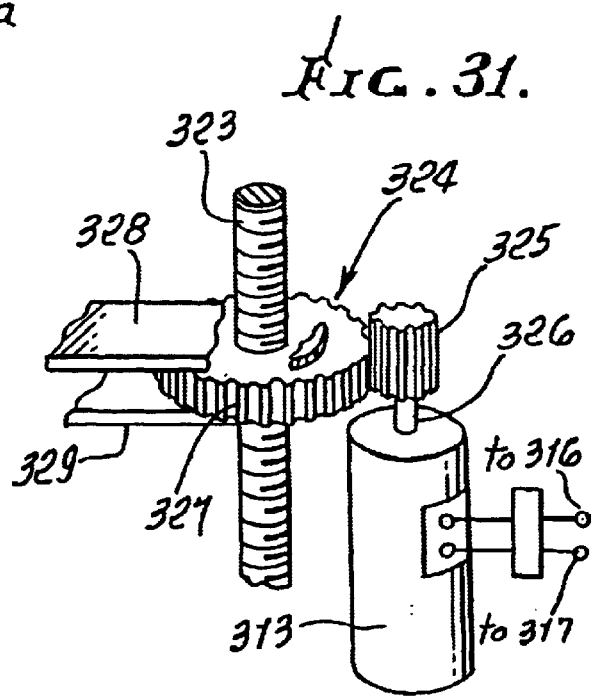

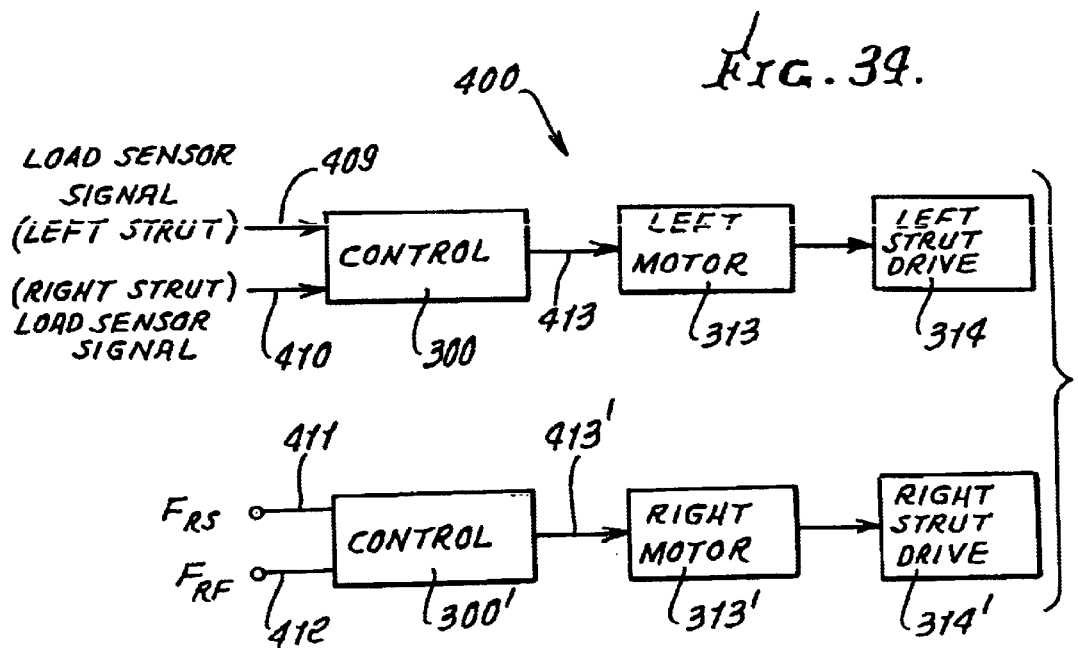
Fig. 34.
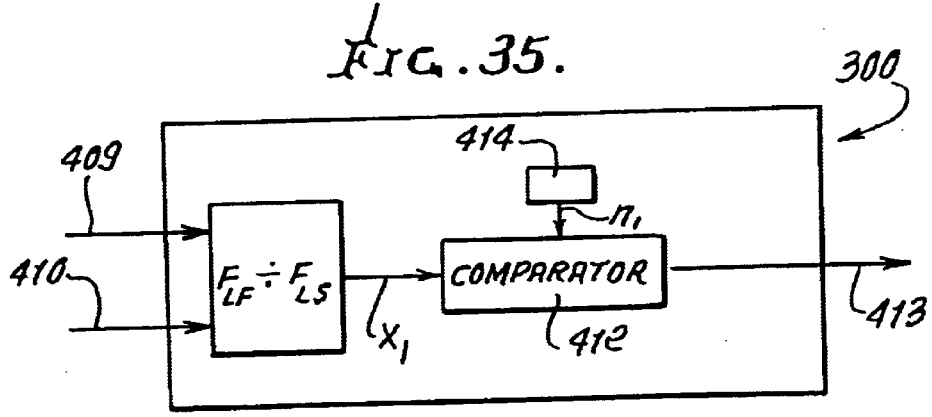
Fig. 35.
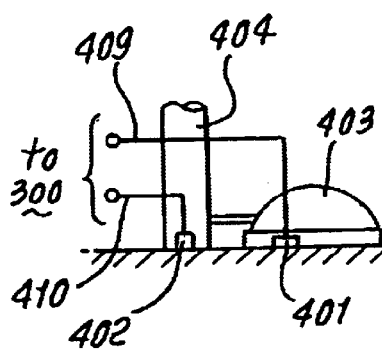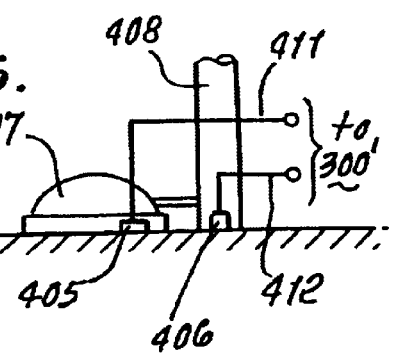
Fig. 36.

WALKING ASSISTING APPARATUS

BACKGROUND OF THE INVENTION

This invention relates generally to apparatus to assist walking, and more particularly to such apparatus which functions to assist in transportation of carried weight, and/or body weight in the direction of walking, in response to treading.

When a person stands, walks, or runs, the force the foot experiences at the ground is transmitted (less the leg weight) to the hip/leg connection. A strut going from ground (slaved to the foot-shoe location) to the hip joint could take some of the load and thus the person would experience less load on the lower limbs and joints. The upper part of the leg-strut cannot be positioned within certain regions at the hip joint, but in the practical case being. positioned in the near vicinity proves satisfactory. If the operator is carrying a heavy back pack, the upper part of the leg-strut can couple directly to the back pack and, by supporting some or all of the back pack's weight, decrease the hip joint load.

Further, a person running or walking ordinarily has an unloaded leg and foot, and one loaded leg and foot. The unloaded leg/foot is bent to decrease its length and has the foot off the ground. What is needed is a leg strut on that leg/foot free to vary in its length-without appreciable resistance. Thus the free (unloaded) leg operates as though there were no leg-strut. However, the load on the loaded leg is decreased by whatever amount its leg-strut carries.

SUMMARY OF THE INVENTION

It is a major object of the invention to provide struts with lower end portions that couple to legs or feet of a human who is walking or running, or climbing, or descending or jumping down, the upper end portions positioned to a rack or structure secured to the upper body, the struts directly transmitting backpack or backrack loading to the ground, i.e. independently of the carrying force of the user's legs.

Another object is to provide a load bearing flexible joint connection between the backpack or backrack and the upper end of a strut, and two such joints may be provided, one for each strut. In addition flexible joints may be provided to couple the lower ends of the struts to the user's shoes or boots.

Another object is to provide a shoe force sensor controlling a lock between relatively movable upper and lower struts, permitting the user's leg and associated struts to relatively extend or retract freely when the user's foot is lifted relative to ground so that shoe sole transmission of strut transmitted loading is zero or less than about 3 pounds; and wherein the lock operates to lock against relative shortening of distance between the top and bottom of the upper and lower struts when the user's leg is vertically loaded to the shoe sole force exceeding about 3 pounds. The lock does not inhibit strut lengthening.

A further object is to provide extensible struts that extend and retract in distance, as in telescoping, or which extend and retract in an articulated or hinged mode.

An additional object is to provide a controlled brake that allows the struts to be retracted against an imposed braking force when the user's leg is bent or flexed (as at the knee) to an extent that the flexed knee is 1 inch or more ahead of straight leg position.

The following are considerations to be taken into account, or that may be taken into account. The details of the force the foot exerts on the ground throughout a walking or running gait over rough ground are complex—flat foot, mostly heel, mostly toe, heel raised so only front of foot contacts ground, etc. The leg-strut, for simplicity, contacts the ground at only one convenient location, and has some vertical "slop" (i.e. looseness) in its vertical connection to the shoe and vertical "slop" in its connection to the operator's body through the backpack rack and the connection of the rack to the body. If the lower strut end connects to the shoe more rearwardly than depicted here, some greater vertical "slop" is appropriate so the strut still provides support as the heel is raised while the toe still contacts the ground.

It is another major object of the invention to provide, apparatus to assist human walking or running, that comprises in combination:
 a) first and second strut members that are relatively movable, and adapted to support body associated loading, where such loading may comprise loading from a carried pack, from a backpack, or from the human body, or any combination of these,
 b) first means to transmit said loading and comprising at least one of the following:
  i) a seat,
  ii) a rack such as part of a backrack,
  iii) a pack, such as part of a backpack,
  iv) an attachment connectable to the human body, such as a strap or straps, a harness, or other connection,
  v) a hand grip,
  vi) a support such as a crutch top,
 c) second means to connect the second strut member to foot or ankle apparel such as a shoe worn by the human,
 d) and third means to alternately block and unblock such relative movement of the strut members in response to step-by-step treading to assist in transport of said loading in the direction of walking.

It is another object to provide a latching interconnection of the strut upper and lower members, responsive to treading. For this purpose, a ground engaging plate member may be hinge connected (i.e. "slaved") to the user's shoe, and a link may connect that plate with a latch, to provide latch response to treading.

A further object is to connect the strut upper member with a user's backpack rack, strapped (i.e. "slaved") to the user's back, for load transfer purposes. Both left and right strut extensible upper members may be connected to that rack, to directly transfer loading to the ground.

It is a further object of the invention to provide such first means to comprise an attachment to attach to the human body, that attachment having load transfer association with said first member. The attachment is typically configured to attach to the human shoulder area, and may comprise a rack as part of a backpack. The second means may advantageously comprise a bracket adapted for connection to the shoe, the bracket having load transfer association with the second member. Such a bracket may be connectable to a human shoe.

Yet another object is to provide a control to controllably effect alternate blocking and unblocking relative movement of the overall length defined by the strut members in response to such walking. One highly advantageous form of control includes generally longitudinally spaced shoulders such as teeth on one of the members, a shoulder engaging and disengaging part, and a load transfer member that extends generally lengthwise and between said second means (slaved to the foot) and that part.

A further object includes provision of guides on the two longitudinally extending strut members to guide relative longitudinal movement thereof. In this regard the members may have telescopically sliding interfit.

These and other objects and advantages of the invention, as well as the details of an illustrative embodiment, will be more fully understood from the following specification and drawings, in which:

DRAWING DESCRIPTION

FIG. 5a is an enlarged section showing in side view an alternate latch mechanism; FIG. 5b is a view taken on lines 5b—5b of FIG. 5a; and FIGS. 5c and 5d are similar views during stepping;

FIG. 6 is a schematic view of operating elements;

FIG. 6a is a fragmentary elevation showing a brake mechanism;

FIG. 7 is a fragmentary elevation showing an actuator link extending from a lower plate into the interior of the lower strut member;

FIG. 13 is a perspective view of a brake system to control strut extension and retraction;

FIG. 14 is a frontal view of the FIG. 13 system;

FIG. 15 is a frontal view of part of the FIG. 13 apparatus;

FIG. 16 is an elevation showing application of the FIG. 13 system to a strut and backpack assembly;

FIG. 17 is an enlarged view of the shoe and lower strut connection; as seen in FIG. 16;

FIG. 18 is a view taken at right angles to FIG. 16;

FIG. 19 is a schematic view of fore and aft adjustment of strut to shoe connections;

FIG. 20 is an enlarged view of strut to foot connection, and a control, as also seen in FIG. 18;

FIG. 21 is an elevation showing use of a flexible cable link in the FIG. 16 system;

FIG. 22 is a perspective view of a shoe twist-on connection to a platform usable in the strut to shoe connection system;

FIG. 22a is an elevation showing a lengthened strut lower end; and a larger sole plate;

FIG. 23 is a perspective view of a torsion bar system applicable to the strut system referred to, and useful to conserve energy otherwise expended during extreme striding;

FIG. 27a is a perspective view of the lever and brake of FIGS. 26 and 27;

FIG. 28 is an elevation showing a stretchable cord system applicable to user's legs to conserve energy, in a manner similar to FIG. 23, and also usable during striding at times when the described strut systems are employed;

FIG. 29 is a plan view of a'stretchable cord system applied to a user's legs;

FIG. 30 is an elevation showing control of strut extension and retraction by use of a controllable jack screw type mechanism;

FIG. 31 is a perspective view of gearing as employed in FIG. 30;

FIG. 34 is a block diagram of a control system for both left and right sets of struts;

FIG. 35 is a block diagram showing details of a block used in FIG. 34;

FIG. 36 shows use of load cells at the user's foot and at the lower end of a strut, for control purposes, for both left and right strut systems, and as related to FIG. 34;

DETAILED DESCRIPTION

Figure 1:
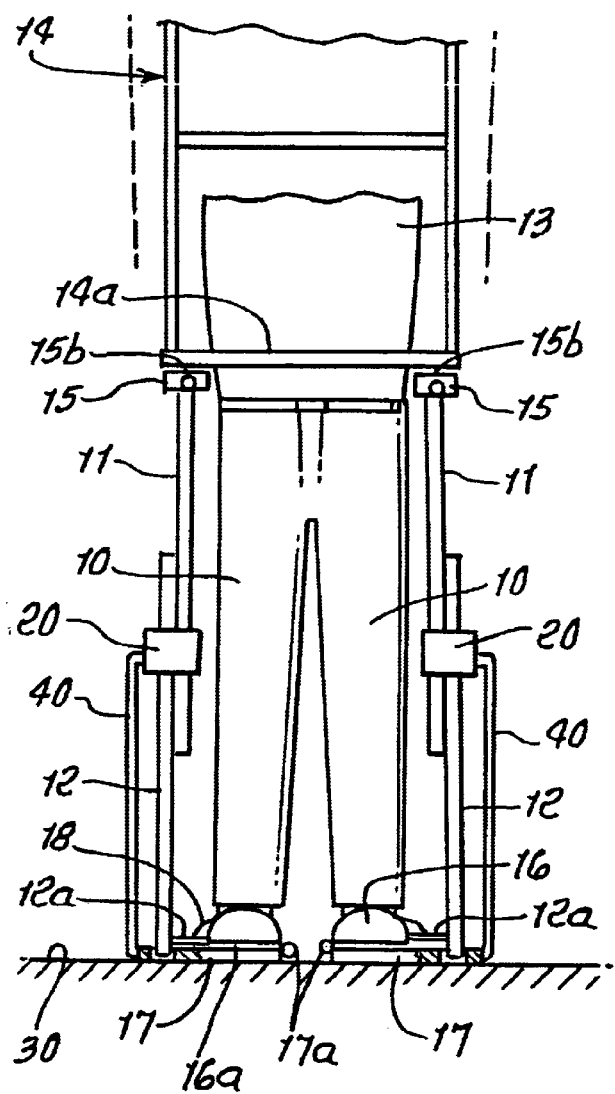
FIG. 1 is a frontal elevation showing two strut member assemblies coupled to the user, as via ground engaging plates coupled to the user's footwear.

Referring first to FIG. 1, first and second longitudinally extending members are associated with each of a human user's legs 10, and are selectively relatively movable, lengthwise longitudinally. As will be seen, they are adapted to support body loading, as during walking. See for example upper strut member 11, and lower strut member 12. Two pairs of such members 11 and 12 may be provided, one associated with each leg 10.

Figure 4:
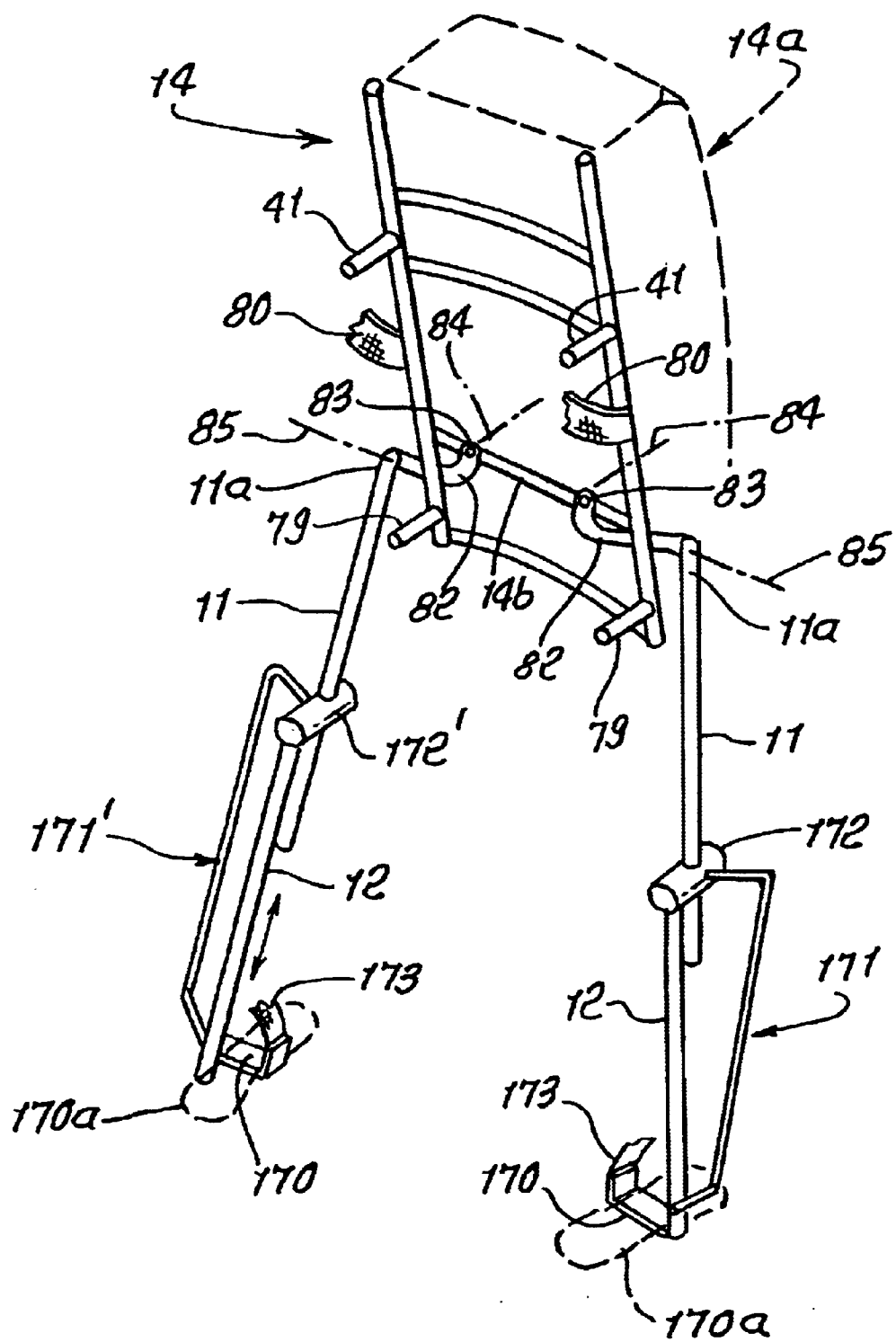
FIG. 4 is a perspective schematic view showing a backpack rack connected to upper members of two extensible strut assemblies that couple to the user's footwear.

First means is provided to transmit body loading between the first strut member 11 and the human body, as for example at the torso 13. One such means is a brace such as a backpack rack 14 connected at 14a to the user's waist as by a strap or straps, and a connection bracket or brackets 15 located generally laterally at the top of each strut member 11, and. joining at 15b to the rack whereby loading is transferred from the mid-body to the members 11. See also FIG. 4, showing optional hand holds and armpit supports 41, on the rack to transfer body loading to the rack. Also shown is a shoulder strap 80 to attach the rack to a human torso. Rack 14 transfers body loading to the brackets 15 and then to the strut members 11, in FIG. 1. In FIG. 4, L-shaped lever arms 82 connect the tops of struts 11 to a pivot or pivots, 83, at rear regions of the rack, the pivots spaced from a vertical center line, corresponding to lateral spacing of hip sockets from the body center plane.

Referring to FIG. 1, a plate 17 is hinged at 17a to the bottom edge of the shoe 16a, so that the plate moves downward when there is no downward force on the shoe sole as when the sole is lifted. The plate is positioned to be used in controllably locking and unlocking of the elongation control mechanism 20 that controls elongation of the leg struts 11 and 12. Connector rods 40 connect the plates to the control mechanism 20. Downward swinging of each plate 17 may be limited by the hinge 17a, or by a strap 18 connected to the shoe.

The bottom of the leg strut 12 is loosely mechanically connected, as at 12a to the shoe, so that when the shoe is on the ground, the bottom of the leg strut is also on the ground. Second means is thereby provided to connect the second strut member to foot or ankle apparel worn by the human. See FIGS. 7 or 37 for a representative mechanism.

Third means is provided to alternately block and unblock relative lengthwise movement of strut members 11 and 12 in response to step-by-step treading, to assist in transport of body weight of the human in the direction of walking. Such third means is schematically shown at 20 in FIG. 1, and comprises a clutch or latch mechanism which is responsive to the user's treading, accompanied by up and down leg movement.

Figure 2:
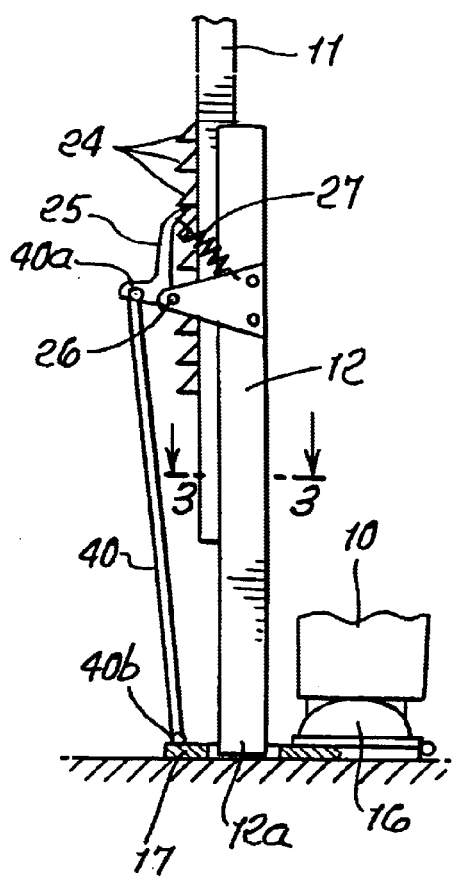
FIG. 2 is an enlarged view showing a latching mechanism operable to couple and de-couple upper and lower strut members that slide relatively up and down in response to treading, the latch controlled by a link coupled to footwear.
Figure 3:
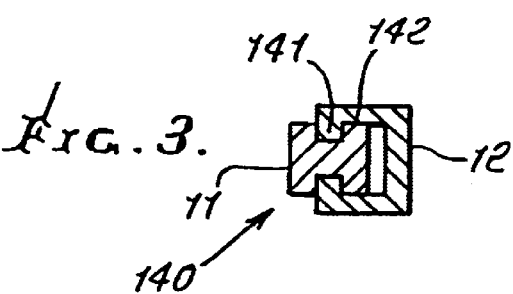
FIG. 3 is a section taken on lines 3—3 of FIG. 2.

A more detailed schematic representative of one such clutch is seen in FIGS. 2 and 3, other forms of clutch or latch being usable. As thus shown, a series of ratchet teeth 24 are carried by one of the members 11 and 12, as for example member 11, the teeth arranged in longitudinal sequence along 11. A latch dog 25 in the form of a bell crank is pivotally carried by the other strut member 12, as at pivot 26, to engage and disengage the ratchet in response to step-by-step walking. In this way, the members 11 and 12 are interconnected so as not to be relatively longitudinally movable during shoe support on the ground, thereby to transfer body loading to the ground in by-passing relation to the user's leg; and so as to be relatively longitudinally movable and collapsible during shoe disengagement with the ground as during lifting and forward movement of the user's lower leg, as during stepping motion.

During such leg lifting, plate 17 pivots relatively downwardly, connecting link 40 moves relatively downwardly, and bell crank 25 rotates counter-clockwise to disengage the ratchet. A spring 27 (or torsion spring) is shown for urging the dog in a clockwise pivot direction tending to engage the ratchet, at times when the user's shoe 16 engages the ground causing plate 17 to flatly engage the ground.

Link 40 is pivotally connected at 40a to the bell crank, and at 40a to plate 17.

Guide means in the form of tongue and groove elements 141 and 142 facilitate relative lengthwise sliding interfit of the members 11 and 12 as indicated 140 in FIG. 3. A corresponding latching and unlatching mechanism 20 including elements 11, 12, etc., is applicable to the strut members adjacent the user's other leg as shown in FIG. 1.

FIG. 4 shows a backpack rack 14 operatively connected to left and right upper struts 11, in such a way that twisting of the rack and pack (indicated at 14a) along with the wearer's torso, relative to the struts and vice versa is accommodated. See connector levers 82 pivotally connected to rack bar 14b to swivel at 83 about front to rear axes 84; and pivotally connected to strut 11 upper extents 11a, to allow swiveling about side to side axes 85. Axes 84 are in or substantially in the planes of the user's hip joints. Such accommodated twisting enhances comfort and ease of use of the apparatus. Straps 80 connect the rack to the user's body; and hand holds are provided on the rack at 79.

Lower struts 12 are controllably movable up and down relative to upper struts 11. The actuating mechanism to effect the control can involve the following: the user's shoes indicated at 170a are connected to plates 170, and may be strap-connected thereto, at 173. As the user's left foot (for example) steps down on plate 170, an actuator 171 responsive to plate 170 position operates clutch unit 172 to lock strut 12 to strut 11, shown as extending to that actuator. Meanwhile, as the user's foot is raised to step forward, the right plate 170 is raised, causing actuator 171' to unlock clutch 172', allowing strut 12 to slide upwardly relative to 11.

In a modified apparatus of FIGS. 5a and 5b, plate 17a supports the user's shoe 16a, and a strap 200 extends over the shoe to retain the shoe to plate 17a. The plate 17a has pivoted connection via horizontal shaft 201 to an upright member 202 on auxiliary plate 17b, whereby plates 17a and 17b move up and down together with the user's shoe, but member 202 and plate 17b can pivot about the horizontal axis of shaft 201. Shaft 201 is connected to upright flange 17a' on plate 17a.

Lower strut 12 has a lower lateral extension 12a located above plate 17b, and also pivotally connected to shaft 201. In FIGS. 5a and 5b both plates engage the ground 199 and a rod 28 operates clutching or latching mechanism indicated at 204 to lock struts 11 and 12 together to transfer weight to the ground as during the time that the user moves his body forwardly while his foot remains supported on the ground, as via plate 17a.

Latching mechanism 204 comprises a locking plate 205 loosely pivotally attached at 206 to the upper extent of strut 12 as via a rod 210 carried by 12 and projecting through end 205a of plate 205. Plate 205 forms an opening 206a through which upper strut 11 extends, just above the upper end 12b of tubular strut 12. Strut 11 can slide relatively up and down in strut 12; however, in FIG. 5a, plate 205 is pivoted counter-clockwise so that plate edge 205c jams against the side of strut 11, holding the struts 11 and 12 against relative endwise sliding. Rod 28 is pivotally connected to and extending between projecting crank end 202a of member 202, and plate 205, at location 205b, to hold plate 205 in the pivoted, or "cocked" position shown. At this time, a spring 27a, extending between member 202 and strut 12 is tensioned.

FIGS. 5c and 5d correspond to FIGS. 5a and 5b respectively, but show the positions of the elements when the user's shoe 16a is raised above ground level, as during stepping. At this time struts 11 and 12 are relatively endwise slidable to accommodate such stepping. At this time, spring 27a pulls or swings member 202 clockwise to the position shown, lifting rod 28 which rotates locking plate 205 to an unlatched or "uncocked" position, relative to upper strut 11. That strut may therefore slide freely up and down through plate opening 206a and within lower strut 12, as during stepping. FIGS. 5a–5d represent a control of strut locking that is a function of the force of the strut on the ground. The previously described mechanisms to control strut locking have made locking a consequence of shoe sole force on the ground. The strut locking apparatus is representative.

Independently of FIGS. 5a–5d, see FIG. 6, a schematic showing of the general mechanism, in which shoe sole force controls strut extension and retraction. As shown, upper and lower struts 11 and 12 are provided, as before. A clutching and de-clutching mechanism is indicated by block 100 encompassing 11 and 12. A control line or rod 101 extends between the user's shoe 102 or shoe sole and the block, to control clutching and de-clutching, in the manner described, i.e. during user's leg stepping, mechanism 100 is de-clutched, allowing relative sliding of strut 12 relative to strut 11; and during shoe 102 engagement with the ground, and body torso movement forwardly, mechanism 100 is clutched or braked, at which time strut 12 is held against sliding endwise relative to strut 11, and the bottom of strut 12 transfers loading downwardly to the ground via the two struts. A backpack frame is indicated by the block 103, to which the upper end of strut 11 is connected; and a block 104 such as a strap connected to 103, transfers body loading to the backpack frame, with appropriate pivots employed to allow body pivoting relative to upper struts 11.

The mechanism 100 may take the form of that described in FIG. 2, i.e. a rack and movable dog; or it may take the form of a strut "cocking" device as in FIGS. 5a and 5c, or a brake such as a coaster brake as used on bicycle rear wheels. Such a brake mechanism 111 is shown in FIG. 6a as carried by upper strut 11, as by a support 112 projecting laterally through an elongated slot 113 in strut 12. The mechanism 111 is connected by link or line 101 to the user's shoe. Mechanism 111 locks to strut 12 during shoe 102 engagement with the ground as the user's body moves forwardly, and unlocks from strut 12 during foot stepping. See also the detailed mechanisms of FIGS. 13–15.

FIG. 7 shows the control link or rod 28 extending within hollow 27 in lower strut member 12, and protruding downwardly to connect to the hinged plate 17.

Figure 8:
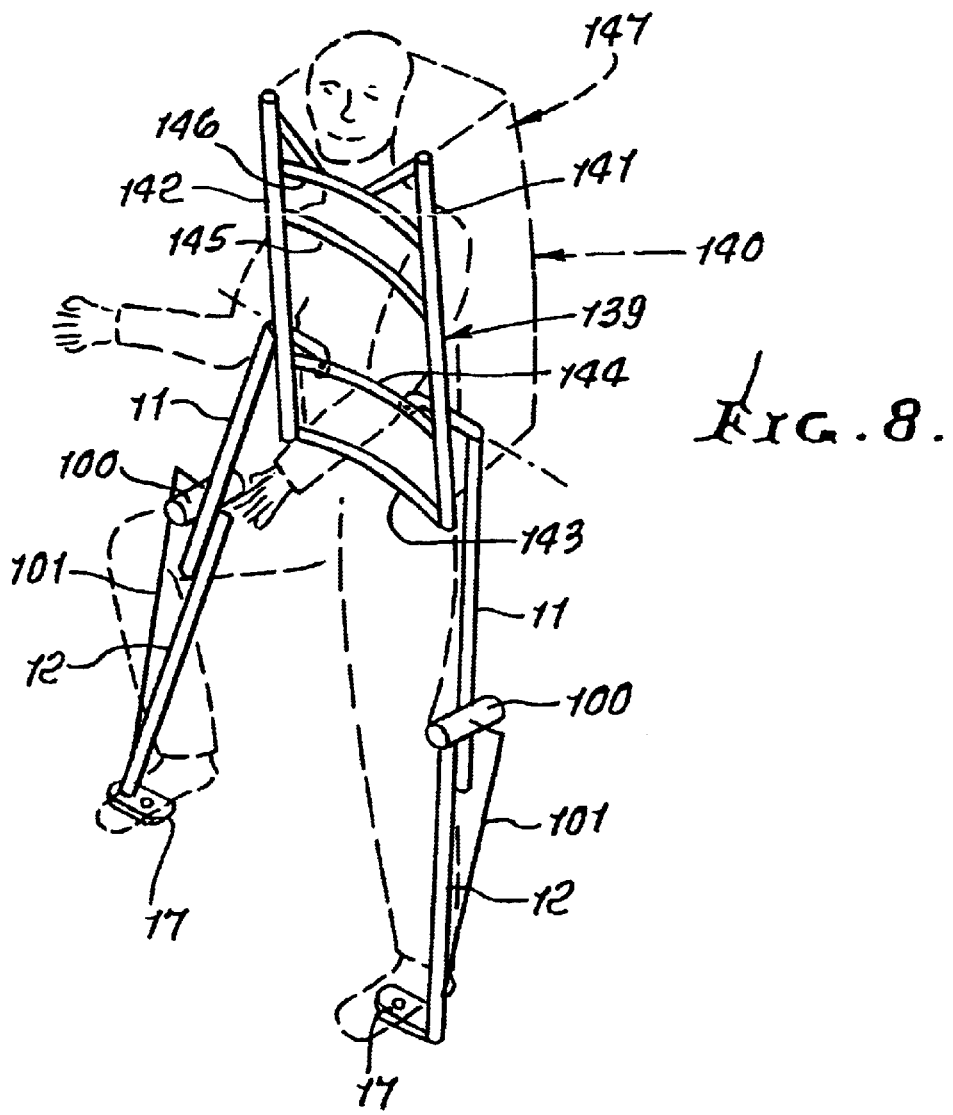
FIG. 8 is a schematic diagram showing apparatus in use incorporating the invention.
Figure 9:
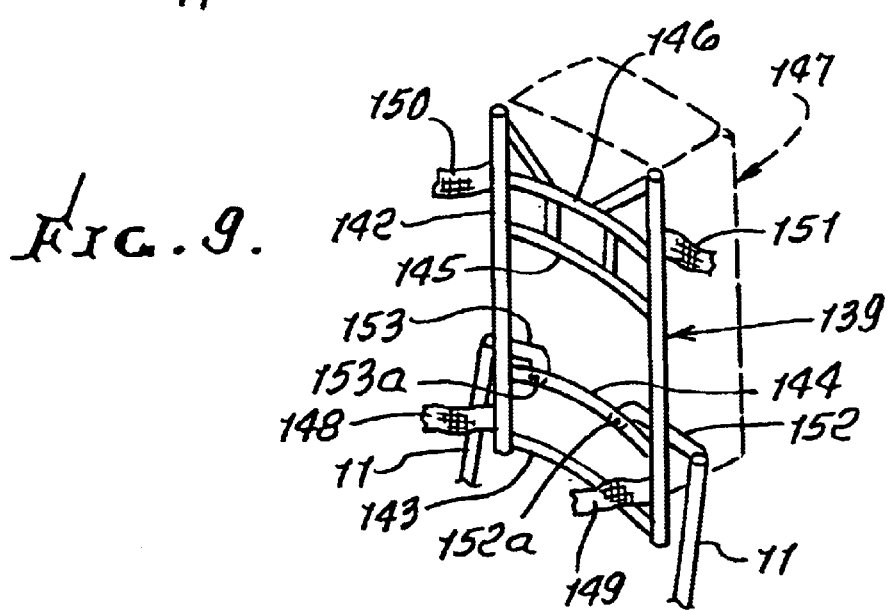
FIG. 9 is a perspective view of a backpack and frame, connected to struts.

FIGS. 8 and 9 show a further modification, employing connection of upper struts 11 to a backpack seen at 140. The backpack includes frame 139 having two spaced apart upright members 141 and 142, interconnected by cross bars 143–146. The pack itself is indicated by broken lines 147 in FIG. 9, and is suitably connected to the frame. Straps 148–151 may be used and have different positions to connect the frame to the shoulders or torso of the user. Upper straps 150 and 151 connect to shoulders and straps 148 and 149 connect to lower torso area such as crotch area. Left and right link type connectors 152 and 153 connect the upper ends of the upper struts 11 to the cross bar 144, and may have pivoted connections at 152a and 153a to the bar 144, providing a certain degree of cushioning of weight transmission to struts 11, during walking. If desired, suitable stops may be provided to limit pivoting of the links, relative to the rack frame. Mechanism associated with the struts 11 and 12 may be as in FIGS. 6 and 6a, with rod 101 connecting the bottom plate 17 to the lock/brake mechanism 100 to control strut 11 and 12 telescoping.

Figure 10:
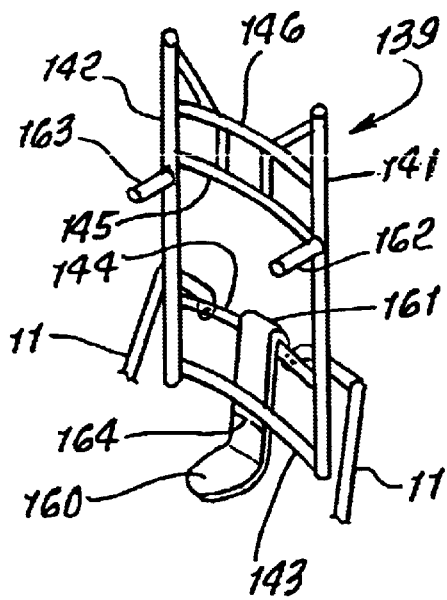
FIG. 10 is perspective view of the FIG. 9 backpack showing added elements.
Figure 11:
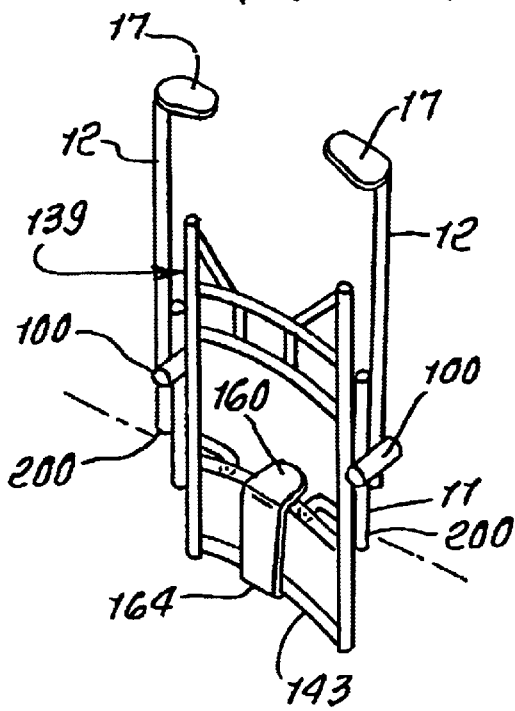
FIG. 11 is a view like FIG. 10, showing the leg struts folded back against the backpack frame for compact storage.
Figure 10A:
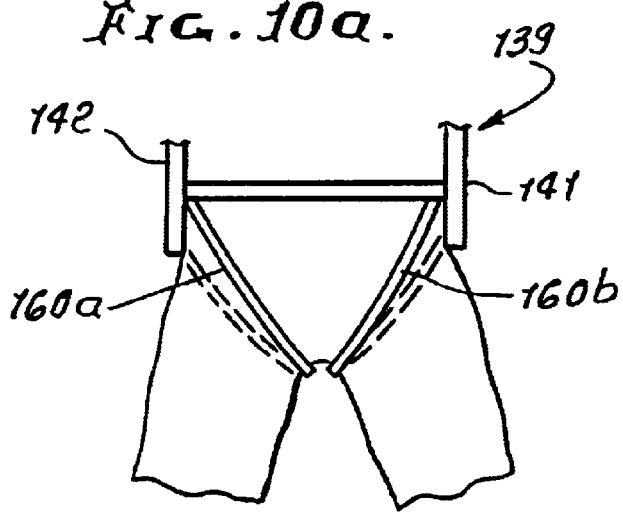
FIG. 10a is a frontal view of a body harness to transfer body loading to struts.

If the operator chooses to have some of the loading supported by the leg struts, a portion of the operator's weight, there are various mechanisms to provide the apparatus, as for example a bigger seat, a climbing harness; a support such as the top of a crutch, and a support like a crutch hand hold. In addition, the belly strap that has positioned the backpack, can be made wider and tighter. In FIGS. 10 and 11 the frame 139 remains the same as in FIG. 9; however in FIG. 10 a bicycle type seat or rest 160 is attached to or suspended from the frame, as at 161, to enable at least some user's weight transfer to the frame, and left and right projections (such as crutch type arm rests, or hand grips) 162 and 163 projecting from the frame enable additional weight transfer to the frame. FIG. 11 shows seat element 160 upwardly collapsed (i.e. folded abut hinge 164) relative to the frame, for storage; and also showing members 11 and 12 upwardly collapsed (pivoted 180° as at pivots 200), for storage. FIG. 10a shows use of climbing harness straps 160a and 160b, connected to frame 139, and about wearer's upper legs.

Figure 12:
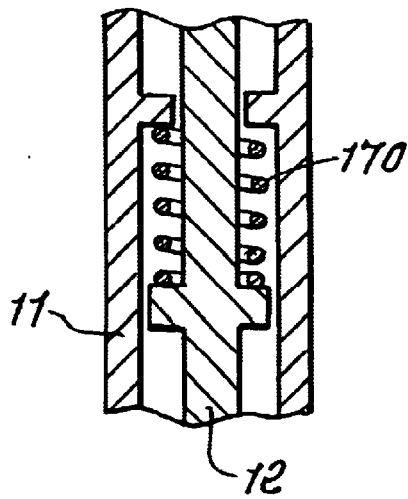
FIG. 12 shows use of a spring to cushion relative movement of struts.
Figure 24:
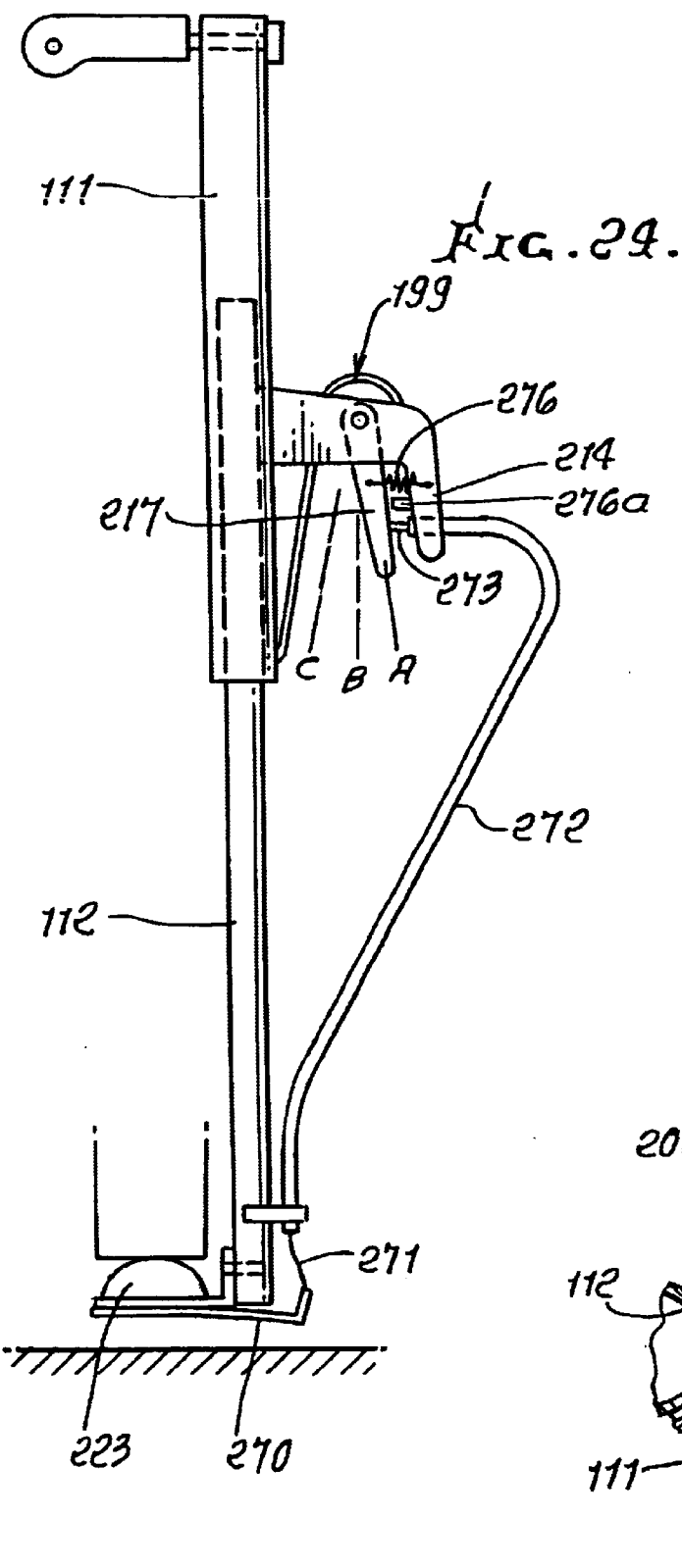
FIG. 24 is a view like FIG. 16, and showing details of use of a flexible cable control link.
Figure 25:
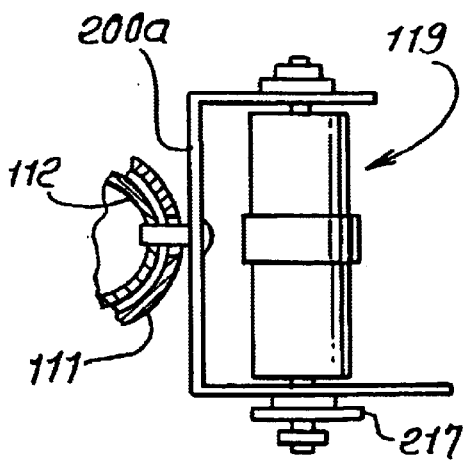
FIG. 25 is a plan view showing a mode of brake connection to a strut.

In FIG. 12 a coil spring 170 is employed to interengage the struts 11 and 12, such as shoulders on such struts, to cushion their relative endwise collapse, as during walking.

Accordingly, first means to transmit body loading between the strut member 11 and the human body may comprise at least one of the following:
  i) a backpack frame
  ii) an attachment connectable to the human torso,
  iii) a seat associated with the frame, or crotch support of climbing harness,
  iv) a grip or grips associated with the frame,
  v) a belt, as referred to.

Operation of a typical device is as follows:
Setup (Example)

The rack-type backpack is affixed to the user in the ordinary way: soft belt around waist/stomach; shoulder straps over shoulders and under arms back to rack, for main support of backpack load. Each strut-leg extends from connection to the rack to (lower end) the outer edge of the corresponding shoe (about at the instep). In other words, the user is carrying a conventional rack type backpack (heavily loaded), to which leg struts have been added to carry some or all of the load. The user moves in the ordinary way, instinctively adapting one's active control system, and limbs, to accommodate the added mass.

Walking
  Conditions

From standing up to a fast walk (about 5 mph), on a surface that in the fore-aft direction is within about 3% (5% slope) of horizontal. Steeper slopes can be handled with shorter steps. (In the crosswise direction the slope can be whatever one can accommodate without any additional load.)

Leg-Struts

The simplest version suffices, (foot load-controlled full lock/unlock). Struts 11 and 12 are unlocked when shoe sole is supporting less than 2 lbs; otherwise locked against shortening. When walking on the level at slow or moderate speed, both struts and the user's legs are operating in, and are equivalent to, a flat-footed gait. As one moves faster, or operates in a gentle up or down slope, the feet will play a more active role, in effect slightly adjusting the length of one's own straight-knee loaded leg. This will have a negligible effect on load power. Because the coupling between the backpack and one's body is rather flexible, one's feet will be operating normally.

Power Required

On firm level ground, the strut supported heavy backpack does not appreciably increase walking power consumption over the zero-load case. At 3° upslope and 6 ft./sec. speed, power for an unloaded 150 lb. person increases by 64 watts (0.086 HP). Adding a 150 lb. backpack also increases one's power delivery requirement by another 64 watts. Carrying oneself at 150 lbs. and a pack at 150 lbs., ascending the 3° slope at 67 ft. forward speed (a fast walk) and 0.314 ft./sec. vertical velocity, achieves an ascent of 1130 ft./hour and costs 0.17 horsepower more than traveling on a horizontal road. During a 3° descent, the 150 lb. strut supported load is delivering power that must be dissipated in the use of one's limbs. Power-wise this is equivalent to descending a 60 (10%) slope without the load attached.

Ascending

Condiitions

Ascending a steeper slope than discussed above, or climbing stairs, or a steep, rocky path.

Apparatus

The same, simplest version suffices (any foot load fully locks the struts from shortening, although extension is not impeded). Both legs can be under load simultaneously.

Power Required

An ascent rate of 1130 ft./hr. (0.31 ft./sec.) requires the same additional human power (beyond ordinary walking at whatever speed one using) as discussed above. One can rest, at each step, without the backpack load tiring leg muscles. The leg force to lift both the user and the pack load needs consideration. By side to side rocking (a natural motion), the instantaneous peak force for lifting the pack load can be decreased, as the lateral body movement can be used to help "lever" the load up. On average one still must provide the same average power for a step cycle.

Descending

Conditions

Descending stairs or steep slope.

Apparatus

As an unloaded leg extends and moves down for the next step, the loaded leg must bend to lower the body. The simple "loaded=locked against shortening; unloaded=unlocked" control that suffices for walking and climbing now may be inadequate. A new control formula is required. The new control should not completely lock the struts to support the backpack load fully, but should support only a portion, say 90%, of the backpack load. There are many possible modes for the control formula. The mode that appears simplest is a "bent knee override of locking". When the knee of the loaded leg is bent more than 1 or 2 inches, the lock serves to brake 90% of the load through struts. One's muscles must support the residual 10%; in descent, the remaining load is dissipated in the brake. Other control options for the switch from full lock to percentage braking can be considered.

Power Required

The "locked" leg compresses with a dissipation brake—such as a friction brake. The dissipation system absorbs the main energy of descent, turning it into heat, as with the brakes on a car. The brake on a coaster bike shows that a small brake can be operationally satisfactory.

Special Considerations

When one's body is also being supported partially by the strut-backpack system, the above "90% of pack load" may be increased to, say 90% of ones weight plus pack load". Such a brake will be fully locked on the loaded leg in most normal walking conditions, and still permit dissipative shortening during stair descent—in other words, no new control system need be switched on.

Running

Conditions

Above 5 mph, the humane gait switches from walking (loaded leg unbent) to running (loaded leg bent). A primary reason for the switch at this critical speed is that the geometric descent rate of body mass with a rearward unbent leg exceeds the descent rate of gravity acting on the mass; one's foot then doesn't connect to the ground firmly. A bent loaded leg at mid-strike (foot under body) changes (reduces) the subsequent geometric descent rate of the body. Also, as the front foot contacts the ground, some bending of that leg decreases the shock.

FIG. 13 shows a braking device 199 as may be used to interlock and release the upper and lower struts 111 and 112. It may be considered as one preferred form of the invention. It includes a U-shaped bracket 200 having two flanges 201 and 202 interconnected by a cross-piece 203. The latter is connected as by fasteners at 204 to the lower strut 112, as via a slot 204a in strut 111. See also FIG. 14. Strut 112 telescopes relative to the upper strut 111. An elongated flexible strap 213 is attached to a cylinder 214 carried by flanges 201 and 202 to be rotatable, as about horizontal axis 215. One end of the typically metallic strap is attached to the cylinder 214, and the strap is wound about the cylinder at 213a and then extends downwardly as shown. The strap lower end is attached at 213b to the lowest exposed part of upper strut 111.

The device 199 incorporates known bicycle coaster brake elements, as within cylinder 214.

The device 199 is accordingly, operatively interposed between the upper and lower struts 111 and 112, to either lock them against endwise telescoping collapse, in which case cylinder 214 does not rotate, or to release them for relative telescoping, in which case cylinder 214 is rotatable. The position of a control lever 217 carried by device 199 at one end thereof, controls the status of cylinder 214 rotatability. Thus, if the lever 217 is not pulled down, as in response to lifting of the user's shoe, then the brake unlocks, and the struts are free to telescope, i.e. the lower strut can lift relative to the upper strut which movement is accompanied by cylinder rotation to wind up the strap. If the lever 217 is pulled down, as in FIG. 15 and in response to user's shoe engagement with a pavement surface, accompanied by down movement of a link 220 to that shoe, the brake locks, and the struts are locked against relative endwise movement that would collapse them. However, the upper strut can still relatively endwise extend upwardly, without constraint, because the flexible strap offers no resistance to movement of connection 213b toward the cylinder 214. Upon release of 217, a coil spring, as at 217a returns the cylinder 214 to the position shown.

FIGS. 16 and 17 show in greater detail the strut arrangement, and connections, when the brake 199 of FIGS. 13 through 15 is employed to control telescoping and non-telescoping of the struts. As seen, the link 220 from the lever 217 is connected to an upright extension 221a of a plate 221 that is connected to a user's shoe 223 to extend at the underside thereof. In FIG. 16, the shoe sole has downwardly engaged the pavement surface 224, so that plate 221 is collapsed against the shoe sole, plate extension 221a is moved relatively upwardly, and up-movement of link 220 allows the lever 217 to move upwardly, as may be urged by a spring arrangement at 226. The brake or latch 199 is therefore locked, whereby the struts 111 and 112 are locked together against telescoping (i.e. strut 111 cannot move downwardly on strut 112), because strap 213 cannot unwind from the cylinder 214 which is locked against rotation. However, the use of strap 213 arrangement allows the upper strut to move upwardly, as referred to above.

In FIG. 17, the shoe and plate have lifted relative to ground surface 224, and the plate extent 221b drops, to lower the upright extension 221a relative to strut 112 and shoe 223; this pulls the link 220 downwardly, unlocking the brake, and allowing the struts to relatively telescope; i.e. the lower strut can be lifted by upward movement of the shoe 223, as during user stepping. Shoe 223 has a loose (up-down) horizontal pivot connection at 261 to strut 112.

A rotary bearing 230 at the upper end of the strut 111 allows its rotation, forwardly and rearwardly (out of the plane of FIG. 16 and relative to the directions of walking or running), about a horizontal lateral axis 231. The bearing is carried at the end 232a of a transverse support member 232, the opposite end 232b of which has pivot connection at 233 to a back pack frame member 233a. The axis of that pivot connection extends forwardly and rearwardly (normal to the plane of FIG. 16) allowing end 232a of member 232 to swing up and down about that axis. Therefore, the struts 111 and 112 have swingability about both lateral and forward axes, to accommodate to user's leg movements. Pivots at 230 and 233 are preferably to the rear of the user's back, but offset from a forward-rearward upright plane through the user's spine, indicated at 234. Pivot 233 is near the spine.

FIGS. 18 and 20 are elevational views taken at right angles to the frontal views of FIGS. 16 and 17. FIG. 18 shows the provision of a vertical slot 236 in upper strut 111, allowing fastening of cross-piece 203 to the lower strut, and sidewardly through the wall of the upper strut. It also allows telescoping of the struts without interference with the brake mounting structures.

FIG. 19 shows a forward-rearward adjustment of the strut 212 relative to plate end 221a and plate 221 and the shoe 233 to which the plate is attached. Note the alternate pivot attachment locations 260, 260a and 260b in 221a.

FIGS. 18 and 20 show an advantageous link and lever connection to the sole force sensory plate 221 that includes front to rear lever 239 to which link 220a is connected permitting it to be a tension member. See also pivots at 281 and 282. Lever 239 is also connected via link 240 to the up-down movable end 221a of plate 221, as shown, and is pivoted at 239a to strut 212. As plate 221 moves up relative to the shoe, lever 239 pivots clockwise to pull link 220a down, causing the brake to lock. A shoe sole downward force sensor may be provided, as at 241. Strut 212 is pivotably connected at 260 to the shoe, to allow forward and rearward pivoting of the strut 212 lower end, relative to the shoe. A flexible cable, indicated at 220a, may be substituted for link 220, and connected to the up-down movable end of plate 221. See FIG. 21.

FIG. 22 shows a shoe sole shaped support 242 for the user's shoe, which releasably locks to the support, as at location 243, as when the shoe steps onto the support, at an angle α, and then is twisted back into alignment with the support, locking the shoe sole to the support. This allows quick disconnect of the struts, for storage or for user sitting. Known devices of this type are employed on bicycle pedals to lock to the bicyclist's shoe. Other elements are the same as in FIG. 20. FIG. 22a shows a forwardly and rearwardly lengthened and curved lower end 212b of strut 212, to provide for strut ground contact as the shoe sole 233a bends, as shown, during walking. The sole force sensor plate can also be enlarged, fore and aft, as indicated at 221c and 221d, in FIG. 22.

In FIG. 23, a torsion bar arrangement 244 resists extreme forward and rearward pivoting of the two upper struts 111 and 111a, in directions indicated by arrows 245 and 246. Horizontal bar sections 244a and 244b extend laterally, and have integral legs 245a and 245b. Forked feet 246a and 246b on the legs fit over and attach to upper struts 111 and 111a, so that the legs swing with the struts. See broken line feet positions 246a' and 246b'. See also the upper forked brackets 248a and 248b on legs 245a and 245b, that clip to the struts at 248a' and 248b' to stabilize the connections.

A radial stud 249 on bar 244b projects through a side wall slot 250 in a sleeve 251 having a bore receiving the end of bar 244a. So long as the struts swing within angle β or angles defined by the width of the slot 250, the torsion bars 244a and 244b do not resist such strut movement. Excess relative swinging of the struts causes the stud 249 to engage the edges of the slot, effectively locking the bars 244a and 244b together, and torsionally energizing the bars to the extent defined by excess angular swinging of the struts, and capturing energy returned to the struts upon reversal of such swinging during walking or running. Thus, energy is saved. Angle β defines the limits of stud rotary travel before the bars are energized. Accordingly, what is provided is apparatus to re-capture energy expended as a result of left and right striding as during running for walking, comprising in combination:

a) a resiliently yieldable element or elements operatively connected to one of the following:
      i) the user's left and right legs,
      i) left and right struts via which backpack loading is transferred to the ground independently of the u user's legs,
    b) and a lost motion component or components operatively connected with the yieldable element or elements to allow unresisted relative striding of the user's legs within predetermined stride limits, and to yieldably resist increased striding beyond such predetermined limits. In this regard the resiliently yieldable element or elements comprise bars, at least one of which is a torsion bar, and the lost motion components comprise tongue and groove components operatively associated with the bars, and interfitting to enable relative movement between interengagement limits.

FIGS. 28 and 29 show use of another device 253 to recapture energy normally expended in runner's leg repeatedly extended movement, and which energy is normally not recovered. As shown, device 253 extends between the user's legs 254 and 255 above the ankles, and is yieldably tensioned during running, such tension being used to assist in leg returning movement from extended positions, seen at 254a and 255a in FIG. 28.

The preferred device includes looping strand sections 253a and 253b looping about the user's legs (and retained against downward sliding); or operatively attached to a boot or boots worn by the runner, and two strands 253c and 253d extending between the user's legs, as viewed in FIG. 29. Strands 253c and 253d may for example comprise elastomeric cord sections 253c40 and 253d' such as "bungee" cords, yieldably tensioned during running if the legs stride beyond limits. Alternatively, strands 253e and 253d may be non-stretchable, and 253e and 253f may be stretchable. Strand extents 253e and 253f may be non-stretchable. Use of such dual strands eliminates torque or twisting exertion on the runner's legs. Alternatives may comprise metallic spiral tension spring sections connected in series with non-stretchable extents 253c and 253f. Typically, only the last 20% to 30% of the stride effects stretching of the bungee cord or cords.

A holder 290 keeps the bungee system from dragging, during use, and may be attached to the wearer as shown at 290 in FIG. 28. It may incorporate a weak tension spring. The loops 253a and 253b are suitably attached to the user's legs, for positioning.

As will be seen, a knee operated lever to effect partial braking can be provided, allowing the knee to flex a bit, as the other leg steps lower.

FIGS. 24 to 27a show one form of device, including a lever 260, that controls the coaster brake mechanism 199 (as when a load is transmitted to the shoe sole), to be either locked, or set to apply a selected braking force, as the user's knee 261 (see FIG. 26) bends or flexes, say over 2 inches. In other words, the braking force acting to lock the struts is responsive to user's knee position or position of the leg near the knee. The lever may be pivoted at 262 to the cross-piece 200a of bracket 200. Lever positions are shown at α, β and ∂. At position β, the knee is bent 2 inches, as at knee position 261a in FIG. 26.

Motion of the shoe plate 270, as described above is shown in FIG. 24 as transmitted by a flexible cable 271 in a flexible sheath 272 to a plunger 273 carried by an arm 274 rigidly attached to bracket 200. Motion of the plunger is transmitted to the brake lever, as indicated at 217 (part of brake 199), to override lever controlled actuation (displacement) by the knee. A tension spring 276 tends to keep the lever 217 at position A, i.e. against stop 276a. When the force from the shoe sole is for example over 4 pounds, moving the plate 270 up to adjacency to the underside of the strut, as by stepping on a surface, the lever 217 is moved (by the cable and plunger) to position C, locking the struts together via mechanism 199. Plate 270 corresponds to plate 221 referred to above.

Figure 26:
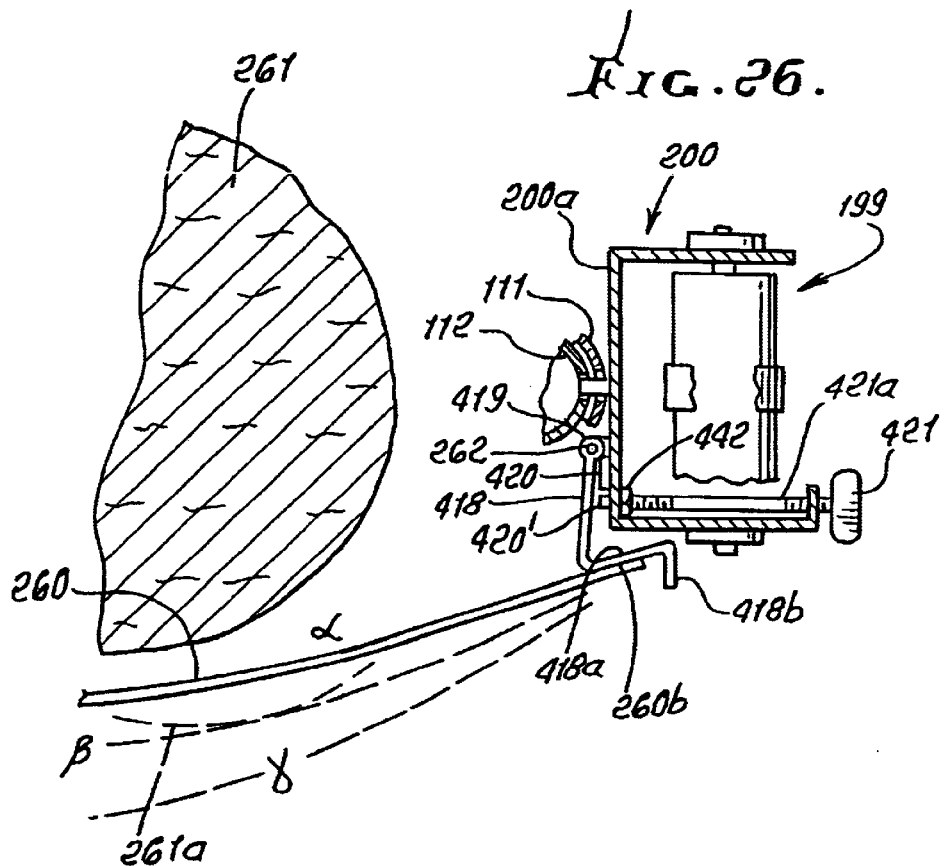
FIG. 26 is a plan view showing use of a lever responsive to changes in flexed knee position to control a brake of the type used in FIG. 16.

Referring to FIGS. 26 and 27a, the knee lever 260 is attached at 260b to a plate 418. Specifically, plate 418 is connected via hinge 419 to a plate 420 attached to bracket 200. The plate 418 has a bent portion 418a to which the lever 260 is attached, and a further bent portion 418b, provides an abutment. Accordingly, lever 260 swings about an axis defined by hinge 419, and perpendicular to the plane of FIG. 26. A stop 420' limits counterclockwise swinging of the plate 418, and it is preferably adjustable, as by rotation of a thumbscrew 421 to control the lever root end position indicated at β; however, the lever can be made of a material to permit its further forward resilient flexing by the user's knee.

Figure 27:
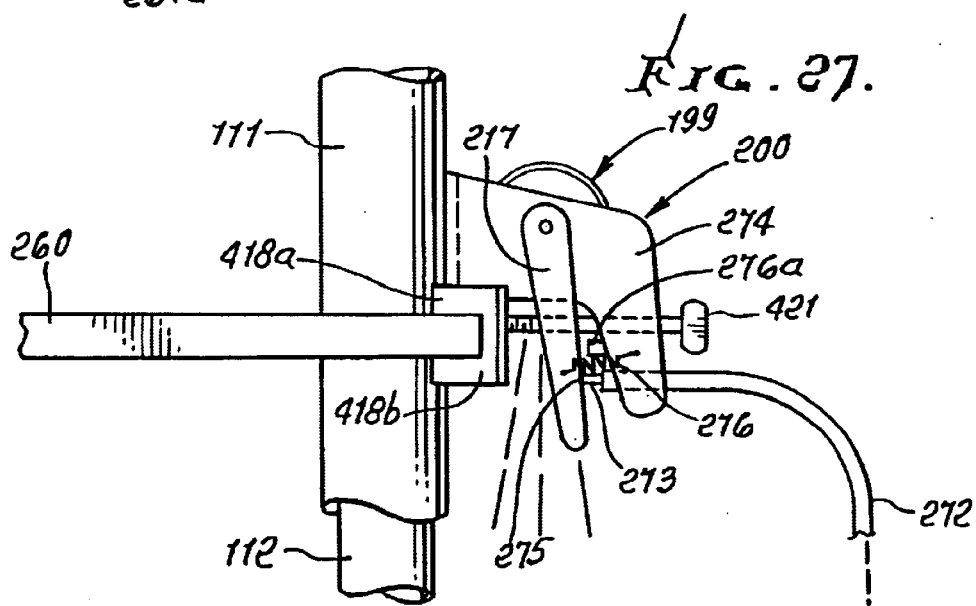
FIG. 27 is a front view of the lever and brake, of FIG. 26.
Figure 32:
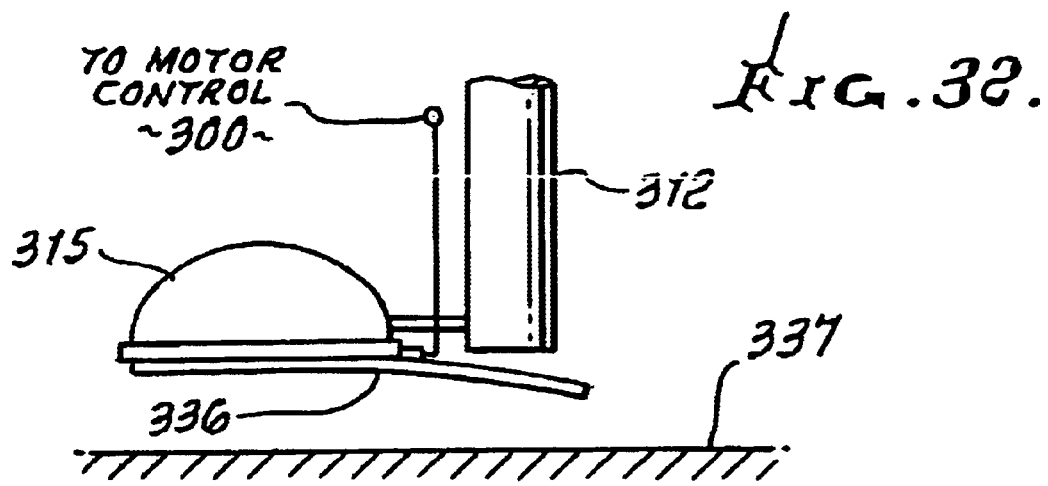
FIG. 32 is a view like FIG. 17, showing another type control.

It will be seen that the position of the further bent hinge portion 418b, or abutment, to provide a limit to leftward movement (swinging) of the brake control lever as seen in FIGS. 26 and 27, will be understood from the following:

i) At position A of brake lever 217, that lever is seen as spaced from abutment 418b in FIG. 27, whereby the brake-lock device 199 is in fully unlocked position or mode, and there is no foot force or position induced extension of plunger 273.

ii) If the user's leg is straight and knee unbent, corresponding to user's shoe engagement with the ground, up-force in the cable 271 displaces plunger 273 leftwardly and lever 217 to position C, and full locking of the brake 199 occurs. The plunger cannot push lever 217 leftwardly beyond C position, because braking in 199 prevents it. Knee lever 260 and abutment 418b do not limit lever 217 at this point, because knee 261 does not engage 260.

iii) If the user's leg is bent beyond about 2 inches at the knee, the lever 260 is knee engaged and typically moves to position β, plate 418 engages stop 420', and the abutment 418b is moved to the right in FIGS. 26 and 27 to block leftward displacement of the lever 217 beyond position B. This corresponds to a reduced braking force transmitted to the struts 111 and 112 to resist but not totally block their relative telescoping movement.

FIG. 26 shows provision of an elastic stop nut 442 through which the lever adjustment screw threads, to positively position the screw terminal 420, for control of lever 260 position β.

FIGS. 30 and 31 show an electrically operating control device 300 as may be used to control endwise relative extension and retraction of upper and lower telescoping struts 311 and 312. It includes an electrical motor 313 carried by one of the struts (upper strut 311 for example) and a drive 314 operatively connected between the motor and the other strut (lower strut 312 for example). The system is organized so that as the motor produces motion in one direction (for example clockwise rotation), the struts relatively extend; and when the motor produces motion in another direction (for example counterclockwise rotation), the struts relatively retract. Control input to the motor, as from the user's shoe, or foot zone, serves to control operation of the motor; thereby, and referring to FIG. 33, when the user's shoe or foot 315 is lifted, a sensor 316 at the foot zone senses such lifting (plate 336 drops below the sensor 316, as shown) and signals the motor to effect relative retraction of the struts; and when the user's shoe or foot is placed on the ground or support surface 337 the sensor senses such placement (as by plate engagement with the sensor) and signals the motor to effect relative extensions of the struts. Such extensions may be controlled to a predetermined first limit corresponding to the user's full leg straightening, as during load bearing during walking, while the other foot is lifted and moved forwardly. In addition, and if desired, the relative extension of the struts may be interrupted at a second controlled i.e. lesser limit at which the struts have overall length corresponding to the user's less than full leg length straightening, as during knee flexing during a step down to a stair or off a curb, to support leg loading with the knee partly flexed. A second sensor 317 may be provided (see FIG. 33) to sense such knee flexing, and may be positioned adjacent the user's knee joint, as at the rear of the knee, to sense interrupted flexing, as during a step down, and to signal the motor to relatively position the struts (as to a selected point between their full retraction and full extension).

Referring back to the FIGS. 30 and 31, electric motor 313 may be of rotary type, with its casing attached via brackets 320 and 321 to the side of strut 311, over its upper end. A lengthwise extending opening 322 in the side wall 322a of the upper strut allows such bracket attachment. An elongated high pitch screw 323 extends parallel to strut 311, and has its lower end anchored at 323a to strut 311, and its upper end attached at 323b to strut 311.

A nut 324, co-axially threadably connected to the screw, is rotatable by the motor, as via a relatively smaller spur gear 325 on the motor output shaft 326, and spur gear teeth 327 on the nut periphery. Referring to FIG. 31, bearing brackets 328 and 329 located at opposite sides of the nut are connected to the side of strut 312, as shown, via gap 322. Accordingly, as the motor shaft rotates clockwise, the struts relatively extend; and as the motor shaft rotates counterclockwise, the struts relatively retract. Nut 324 rides on screw 323, which moves up and down relative to the nut.

Figure 33:
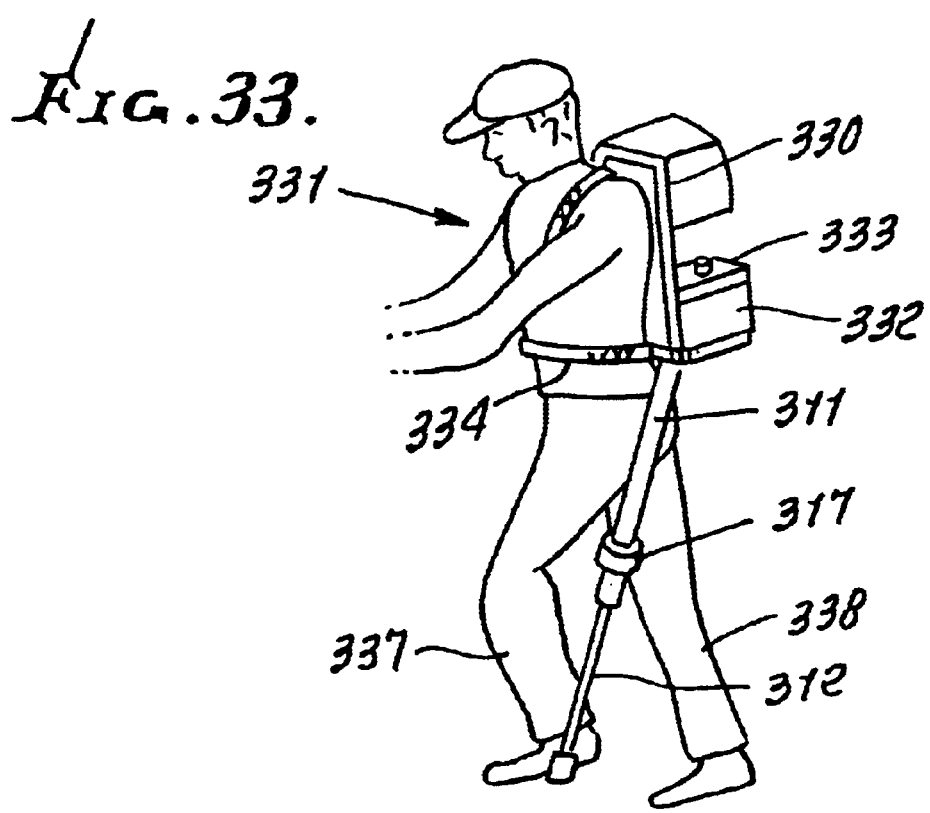
FIG. 33 is a view of a walker, showing direct transmission of backpack loading, via struts, to the ground, with strut movement controlled by or responsive to the user's leg and foot movements.

FIG. 33 shows a backpack rack 330 attached as by belting 334 to the user 331, and carrying an electric battery 332 and control box 333, for controlling and supplying electric current to the motor. One or both of the described sensors may be connected to the control box 333. See also the user's legs 337 and 337. FIG. 33 illustrates the backpack load transmission directly to the struts, to provide a "walking backpack" configuration, which is controlled.

FIG. 34 is a block diagram showing control system 400 for strut positioning in response to sensor signals from a foot load sensor and from strut load sensor, as for each of the left foot and right foot. FIG. 36 shows such sensors as load sensors 401 and 402 at the bottom of the left foot (or shoe) 403 and left strut 404, respectively; and also load sensors 405 and 406 at the bottom of the right foot (or shoe) 407 and right strut 408, respectively. Such sensors respond to downward loading transmitted by the shoes and struts to produce load proportional signals transmitted at 409 and 410 to the control 300 for the drive 314 of the left upper and lower struts 311 and 312 as discussed above, and to produce load proportional signals transmitted at 411 and 412 to the control 300' (like control 300) for the drive 314' of the right upper and lower struts.

Logic in each control provides a proportional comparison as between the two sensor signals, as follows:

$$\frac{F_{LF}}{F_{LS}} = x_1 \quad (1)$$

where $F_{LF}$ = sensor 401 signal proportional to left foot load transmission $F_{LS}$ = sensor 402 signal proportional to left strut load transmission $x_1$ = ratio value and, $$\frac{F_{RF}}{F_{RS}} = x_2 \quad (2)$$

where $F_{RF}$ = sensor 405 signal proportional to right foot load transmission $F_{RS}$ = sensor 406 signal proportional to right strut load transmission $x_2$ = ratio value FIG. 35 shows use of a comparator at 412 within control 300 to compare $x_1$ (for example) with a selected value $n_1$, to produce an output signal at 413 for controlling the left strut's motor 313 such that the drive 314 relatively extends the struts (so that the left struts transmits a greater percentage of load) if $x_1$ exceeds $n_1$; and the motor relatively retracts the struts if $n_1$ exceeds $x_1$, so that the left struts transmit a lesser percentage of the load. Provision can be made for manual or other adjustment of $n_1$, as at 414. The load transmission by the right struts, relative to load transmission by the user's right leg, can be controlled in similar manner. The right strut motor is indicated at 313' in FIG. 34 responding to control signal 413'; and the right strut drive at 314'.

The values $n_1$ and $n_2$ are typically equal or approximately equal, and expressed as follows:

$$n_1 \cong n_2 \quad (3)$$

One condition that $n_1$ and $n_2$ are selected to be unequal, but approximately equal, would be the condition that greater loading is to be borne by one leg than the other, as where one leg is injured. Typical selected fractional values for $n_1$, and $n_2$ are $\frac{1}{3}$, $\frac{1}{4}$, $\frac{1}{5}$, $\frac{1}{10}$, or fractional values between these, etc.

The control signals at 413 and 413' can be made to increase non-linearly so that the more $F_{LR}$ exceeds $F_{LS}$, the faster the motor 300 operates to extend the struts, to restore the desired ratio $x_1$ relative to $n_1$.

Other like sensors can be utilized, as for example bonded wire strain gauges. Such a gauge could be bonded to the side of the lower strut to sense strut strain produced in response to strut load imposition, and thereby produce a signal as a function of strut load. Another such strain gauge could be bonded to the side of a shoe sole to sense strain in the sole produced in response to foot load positions, and thereby produce a signal as a function of foot load.

In the above, it has been assumed that the electric motor associated with each of the left and right strut assemblies is powered by an electric battery or batteries. Other type power sources can be used; for example an electric current generator, suitably driven, can be used in place of a battery. The generator drive can be an engine employing fuel such as hydrogen, natural gas, hydrazine, gasoline, etc. Also, a turbine, or fuel cell, or Sterling cycle engine can be used. Also, force can be supplied by a hydraulic actuator or actuators (piston type or rotary type), the actuator or actuators being electrically controlled. Hydraulic pressure can be supplied by any of the above energy or power producers.

Further, the mechanical movement of each of the left and right strut combinations should be mechanically limited, so that the electrically powered drive cannot relatively extend the upper and lower struts beyond the associated human leg length limits or cannot relatively retract the upper and lower struts beyond a leg compressor limit. Such strut lengthening and shortening limits can for example be provided by the lower and upper ends 322b and 322a of the slot 322 seen in FIG. 30, where telescoping struts 311 and 312 are employed. Other type limits can be provided. Accordingly, the power assist apparatus cannot injure the user's legs by over-extension or over shortening.

In the above description of the apparatus seen in FIGS. 30 through 36, the only situation discussed was where the user's foot or shoe is in forcible ground contact. In this situation, the associated struts 311 and 312 are relatively moved (by the motor and drive to extend or retract the struts) to cause the struts to transmit a selected proportion of the total loading transmitted by both the struts and the shoe or foot (for example, the struts moved in order to transmit 3 (or other multiple) times as much loading on the foot or shoe, to the ground).

Figure 39:
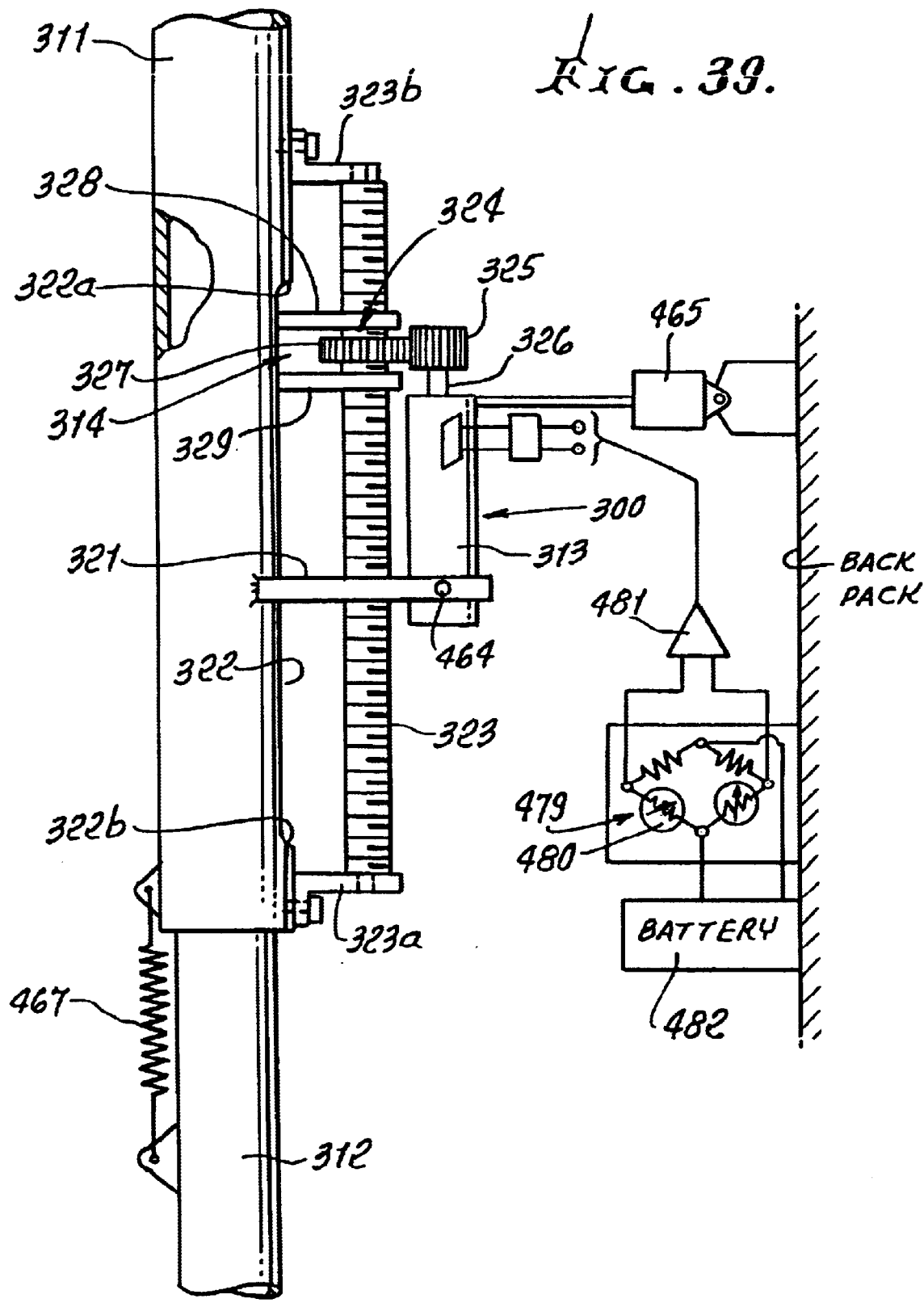
FIG. 39 is a view like FIG. 30, but showing a modification, and use of bridge control.

However, when the user's foot or shoe is lifted so that the foot or shoe and the associated struts do not transmit loading to the ground, the above analysis represented by Equations (1) through (3) does not then apply. As the shoe sole is initially lifted to transmit a lessened leg force to the ground, such as for example 3 pounds or less, a different control system is employed for the motor that drives the struts. Such a control system indicated at 460 in FIG. 39 may employ a solenoid 461 connected at 462 to the motor 313 casing 313a, and operable to pivot the casing to the right, freeing the drive spur gear 325 from the nut wheel 324. Note pivoted supports 463 and 464 for the solenoid and motor casing to strut 311 frame 311c. The screw 323 is then free to move up and down relative to the nut wheel, which can spin in place. The user's leg can then be extended or shortened at will. A spring or other resilient tensioner can be employed to pull up as one or both struts 311 and 312 sufficiently to compensate for the weight of the struts acting to relatively extend them. For example, note spring 467 in FIG. 30 acting to pull up on lower strut 312, relative to the upper strut 311.

Figure 37:
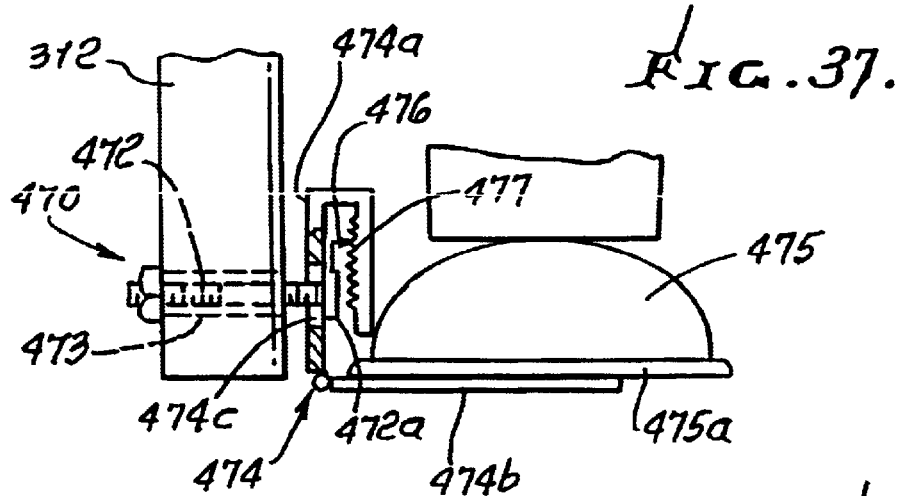
FIG. 37 is a view like FIG. 17, but showing use of a potentiometer control.
Figure 38:
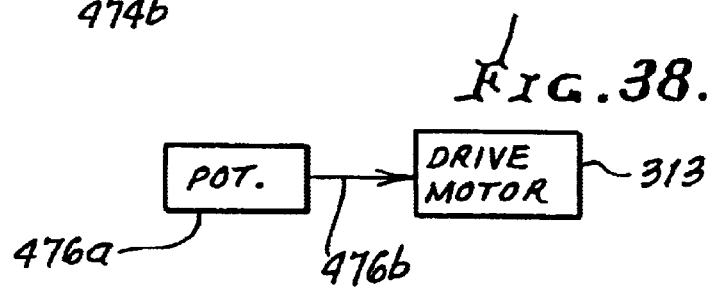
FIG. 38 shows potentiometer output control of a drive motor.

Referring now to FIGS. 37 and 38 they show an additional or auxiliary mechanism 470 employed or coming into effect when the shoe sole transmitted force drops below the lessened value $F_d$. Mechanism 470 operates to maintain a selected vertical position of the lower strut 312 relative to the shoe sole being elevated, i.e. the operative controlling shifts from force transmission sensing mode to strut position sensing mode, when shoe sole transmitted force drops below $F_d$. In the FIG. 37 example, bolt 472 passes laterally and loosely through an opening 473 in the lower end of strut 312. The bolt is attached to upright flap 474a of a hinge 474 as via a vertical slot 474c in the hinge; the other flap 474b of the hinge is attached to the sole 475a of the wearer's shoe 475, as shown. Therefore, strut 312 can move a short distance up and down, relative to the shoe, as limited by upper and lower edges of the slot. A potentiometer wiper 476 is connected to the bolt head 472a, so that the vertical position of the wiper is determined by the vertical position of the strut. The potentiometer slide wire 477 is linear and connected to the hinge flap, and vertical sliding of the wiper against wire 477 varies the output of the potentiometer 476a. The resultant electrical signal at 476b controls the drive motor, as seen in FIG. 38, or as via an electrical bridge network (such as a Wheatstone bridge) 479, seen in FIG. 39, like FIG. 30 and bearing like numbered elements. Bridge resistor adjustment is seen at 480. An amplifier may be employed, as at 481, and battery at 482. Elements 479–482 may be located on the user's backpack, and wiring may extend up the tubing defined by the telescoping struts 311 and 312. The potentiometer and bridge operate to control maintenance of a selected vertical position of the lower strut 312 relative to the shoe sole being elevated, as referred to above. The motor can be pivoted at 464, and swung to the right by a solenoid 465, to disengage gear 325 from gear 327, thereby stopping rotation of 324, to lock the struts in any position.

Figure 40:
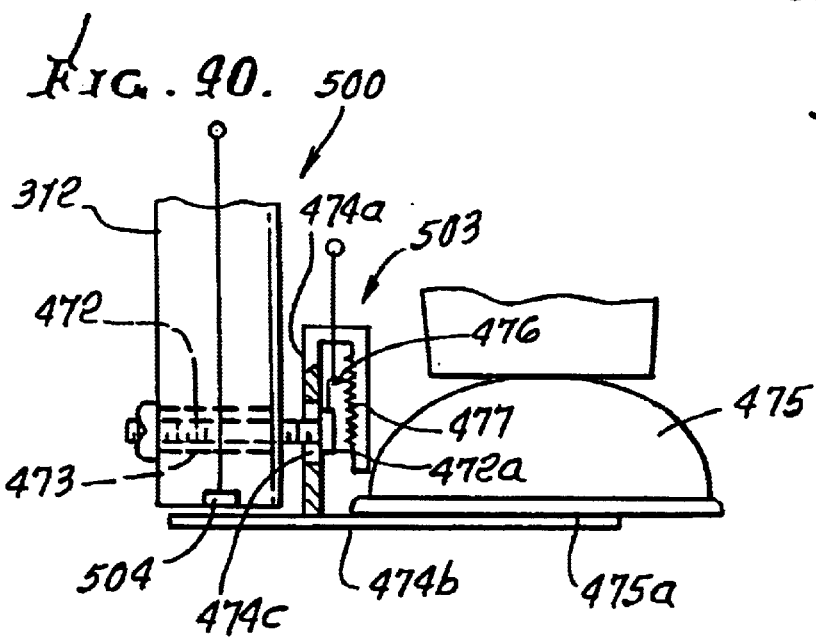
FIG. 40 is another view like FIG. 37, but showing a further modification.

FIG. 40 is similar to FIG. 37, and shows another electrical control system 500 for positioning the lower strut 312 relative to the user's shoe 475. A sensor, such as a potentiometer 503 is employed, in combination with a load cell 504 at the bottom of the strut. There is a hinged plate 474b connection at 475a to the shoe bottom, and to the strut as via a bolt 472 loosely connected to the strut and to upright hinge plate 474a, via opening 474b, allowing limited up-down movement of the strut 312 relative to the shoe. Relative up-down movement of strut is sensed by the potentiometer 503, the output of which is used to control the strut drive (up and down).

The signals from 503 and 504 are such as to maintain, via the control, a predetermined ratio of load transmission $L_s$, via the strut to the ground, and load transmission $L_1$, via the shoe and user's leg, i.e.

$$\frac{L_s}{L_l} = n \quad (4)$$

(for example m=⅓).

Plate 474b is affixed to the shoe sole that extends under the strut and under the load cell 504 and exerts a one pound (or other force) upward force on the strut bottom and hence on the load cell, when the strut bottom parallels the shoe sole bottom. When the strut is lifted, say by ⅛ inch, the plate force exertion on the load cell is zero; and when the strut is lowered, say by ⅛ inch, the plate force exertion on the load cell is say 2 lbs. These forces are negligible when the strut and foot rest on the ground.

When shoe sole force is less than 3 lbs., the controller maintains the strut at 3 times foot load, to maintain the load cell at 1 lb. As the foot moves in air up and down, the strut drive will shorten or lengthen the strut to keep the 1 lb. load.

Figure 41:
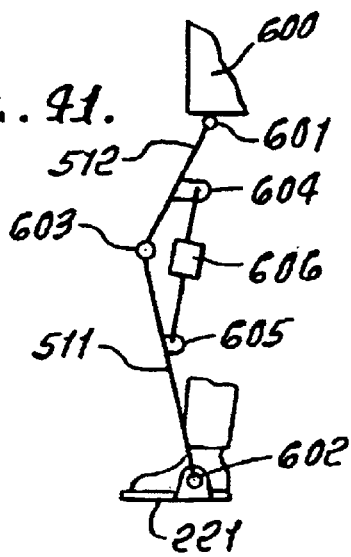
FIG. 41 is a schematic view of struts that controllably flex or articulate, during treading.

FIG. 41 shows upper and lower struts 512 and 511 connected respectively to a backpack 600 and to a user's shoe plate 221, at pivot locations 601 and 602. In addition, the struts are articulated or pivoted at 603 to controllably flex, during walking or running. A motor driven screw and nut drive, as described, or telescopic control links 604 and 605, controlled at 606, can be used to control flexing and locking of the struts, as to accommodate treading, the struts bearing backpack or backrack load.

I claim:
1. Apparatus to assist human walking, comprising in combination:
   a) first and second strut members that are relatively movable, and adapted to support body associated loading,
   b) first means to transmit body loading and comprising at least one of the following:
      i) a seat,
      ii) a rack,
      iii) a pack,
      iv) an attachment connectable to the human body,
      v) a hand grip,
      vi) a body support,
   c) second means to connect the second strut member to a foot or ankle apparel worn by the human,
   d) and third means to alternately block and unblock said relative movement of the strut members in response to step-by-step treading, to assist in transport of loading in the direction of walking,
   e) said second means including a plate having hinge connection to the user's shoe area, to move up and down with the lower strut member,
   f) said third means including a rotary braking latch member operatively connected to respond to ground engagement by the shoe,
   g) said third means also including a link connection between a shoe force plate and the latch member.
2. The combination of claim 1 wherein said first means has load transfer association with said first strut member, whereby loading from the body is transferred to the first strut member.
3. The combination of claim 2 wherein said first means is said attachment which includes a brace connectable to a user's torso.
4. The combination of claim 2 wherein said first means is said attachment which includes a connection between an upper strut member and a backpack frame.
5. The combination of claim 1 wherein said second means comprises a plate having hinge connection to the user's foot area, to hingedly move up and down with the lower strut member.
6. Apparatus to assist human walking, comprising in combination:
   a) first and second strut members that are relatively movable, and adapted to support body associated loading,
   b) first means to transmit said loading and comprising at lease one of the following:
      i) a seat,
      ii) a rack,
      iii) a pack,
      iv) an attachment connectable to the human body,
      v) a hand grip,
      vi) a body support,
   c) second means to connect the second strut member to a foot or ankle apparel worn by the human, said second means comprising a plate having hinge connection to the user's foot area, to hingedly move up and down with the lower strut member,
   d) and third means to alternately block and unblock said relative movement of the strut members in response to step-by-step treading, to assist in transport of loading in the direction of walking, said third means including a rotary braking latch member operatively connected to respond to grand engagement of the shoe, e) and wherein said third means includes an elongated link connection between a shoe sole-plate and said latch member.

7. The combination of claim 1 wherein said third means includes an element to effect alternate blocking and unblocking of relative movement of the strut members in response to said walking.

8. The combination of claim 1 including guides to guide said relative movement of said strut members.

9. The combination of claim 1 wherein said members have one of the following:
   i) a sliding interfit
   ii) a pivoted interconnection.

10. The combination of claim 1 wherein said first means is said attachment that is configured to attach to the human torso.

11. The combination of claim 10 wherein said first means comprises a rack carrying said attachment.

12. In combination, a leg-strut assembly that is lengthwise extensible and contractible, and that at its lower extremity transfers loading to the ground adjacent to a shoe sole of a human operator, and at its upper extremity connects to a weight load some of which would otherwise be carried by the human leg, a latch activator that moves at a fraction of the vertical force between shoe sole and ground and a latch in the form of S rotary braking device, for allowing the leg-strut assembly to extend or contract freely as long as the vertical force on the shoe sole is less than a pre-selected amount but otherwise causes the leg-strut assembly to be stopped from contracting, there being a plate having hinge connection to the shoe sole, and also operatively connected to said latch activator by an elongated link connection between a shoe sole plate and said latch activator.

13. The combination of claim 1 including an associated spring carried by the strut members to cushion their relative movement.

14. The combination of claim 1 wherein said third means comprises a coaster brake type mechanism responsive to said treading.

15. The combination of claim 14 including a plate carried by the user's shoe, and is movable relative to the shoe, and said third means is operatively connected to said part.

16. The combination of claim 15 including one of the following:
   i) a link connected between said third means and said plate
   ii) a cable connected between said third means and said part.

17. Apparatus to assist human walking, comprising in combination:
   a) first and second strut members that are relatively movable, and adapted to support body associated loading,
   b) first means to transmit said loading and comprising at least one of the following:
      i) a seat,
      ii) a rack,
      iii) a pack,
      iv) an attachment connectable to the human body,
      v) a hand grip,
      vi) a body support,
   c) second means to connect the second strut member to a foot or ankle apparel worn by the human,
   d) and third means to connect the second strut member to a foot or ankle apparel worn by the human,
   e) said third means comprising a coaster brake type mechanism responsive to said treading,
   f) and including a part carried by the user's shoe, and which is movable relative to the shoe, and said third means is operatively connected to said part,
   g) and including one of the following:
      i) a link connected between said third means and said part,
      ii) a cable connected between said third means and said part,
   h) and wherein said part comprises a plate carried by the shoe and which flexes relative to the shoe.

18. Apparatus to assist human walking, comprising in combination:
   a) first and second strut members that are relatively movable, and adapted to support body associated loading,
   b) first means to transmit said loading and comprising at least one of the following:
      i) a seat,
      ii) a rack,
      iii) a pack,
      iv) an attachment connectable to the human body,
      v) a hand grip,
      vi) a body support,
   c) second means to connect the second strut member to a foot or ankle apparel worn by the human,
   d) and third means to alternately block and unblock said relative movement of the strut members in response to step-by-step treading, to assist in transport of loading in the direction of walking,
   e) said third means comprising a coaster brake type mechanism responsive to said treading,
   f) and including a strap connected between said mechanism and one of said struts that is movable relative to said mechanism, the strap wrapped about a rotary part of said mechanism.

19. Apparatus to aid load transmission by human leg as during leg movement, during walking, comprising in combination
   a) upper and lower struts that are relatively extensible and retractable, alongside the leg, the struts adapted when extended to transmit body loading applicable to a surface below the user's foot zone, and when retracted to allow leg flexing,
   b) a strut extension and retraction control unit connected to the struts, to control their relative positioning,
   c) and at least one element operatively connected to a retraction unit to control the portion of the struts in accordance with at least one of the following:
      i) user's foot position
      ii) user's foot load transmission
      iii) strut load transmission,
   d) said element including a plate extending under the user's foot position and carried to move downwardly with the lower strut, relative to the user's foot position,
   e) there being an elongated link connection between a foot force plate and said unit.
   f) said retraction control unit includes a rotary braking member.

20. The apparatus of claim 19 wherein said control unit includes positioning components that controllably interengage to allow and to limit strut extension and retraction.

21. The apparatus of claim 19 wherein said control unit including a strut positioner, and an actuator operatively connected to the positioner.

22. The method of transferring human body associated loading to the ground during walking, that includes a) providing left and right pairs of struts, and locating upper end portions of the struts to alternately carry said body associated loading, and
b) effecting guided movement of the struts while selectively transferring loading to the ground via the struts, during movement in a travel direction,
c) and controlling such guided movement in response to shoe up and down positioning during human treading, said controlling including providing a plate hingedly carried by the shoe and which flexes relative to the shoe, and providing an elongated link connection between a shoe force sensor and a latch which is caused to block and unblock relative movement of struts of each pair, said controlling also including operating a rotary braking member.

23. The method of claim 22 wherein said controlling is effected in accordance with one of the following:

i) mechanically ii) electrically.

* * * * *